US008808623B2

(12) United States Patent
Linssen et al.

(10) Patent No.: US 8,808,623 B2
(45) Date of Patent: Aug. 19, 2014

(54) DIAGNOSIS ASSISTING SYSTEM, DIAGNOSIS ASSISTING INFORMATION PROVIDING DEVICE AND COMPUTER PROGRAM PRODUCT

(75) Inventors: Jo Linssen, Kerkrade (NL); Matthias Guhl, Bad Bramstedt (DE)

(73) Assignee: Sysmex Corporation, Kobe (JP)

( * ) Notice: Subject to any disclaimer, the term of this patent is extended or adjusted under 35 U.S.C. 154(b) by 1125 days.

(21) Appl. No.: 12/180,999

(22) Filed: Jul. 28, 2008

(65) Prior Publication Data

US 2009/0069639 A1 Mar. 12, 2009

(30) Foreign Application Priority Data

Jul. 31, 2007 (JP) ................................. 2007-199826

(51) Int. Cl.
*G01N 21/00* (2006.01)
*G06F 19/00* (2011.01)
*G06Q 50/24* (2012.01)
*G01N 35/00* (2006.01)

(52) U.S. Cl.
CPC ...... *G01N 35/00722* (2013.01); *G06F 19/3487* (2013.01); *G06Q 50/24* (2013.01); *G60F 19/324* (2013.01); *G01N 2035/009* (2013.01); *G01N 35/00594* (2013.01)
USPC .................. 422/67; 422/63; 422/64; 422/65; 422/66; 422/536; 436/43; 436/45; 436/46; 436/47

(58) Field of Classification Search
USPC ........................... 422/63–67, 536; 436/43–47
See application file for complete search history.

(56) References Cited

U.S. PATENT DOCUMENTS

| 4,338,811 | A | * | 7/1982 | Miyagi et al. ................ 73/23.36 |
| 5,532,943 | A | | 7/1996 | Asano et al. |
| 6,247,004 | B1 | * | 6/2001 | Moukheibir ..................... 706/46 |
| 6,576,471 | B2 | * | 6/2003 | Otvos .............................. 436/71 |
| 2004/0023404 | A1 | | 2/2004 | Shibata |
| 2004/0265874 | A1 | * | 12/2004 | Binder et al. ...................... 435/6 |
| 2005/0002826 | A1 | * | 1/2005 | Oguni et al. .................... 422/73 |
| 2005/0108216 | A1 | * | 5/2005 | Schramm-Apple et al. ...... 707/3 |
| 2005/0219527 | A1 | * | 10/2005 | Ikeuchi et al. ................ 356/339 |
| 2007/0143037 | A1 | * | 6/2007 | Lundstedt et al. .............. 702/30 |

FOREIGN PATENT DOCUMENTS

| JP | 06-201569 | | 7/1994 |
| JP | 07-057018 | A | 3/1995 |
| JP | 11-326315 | A | 11/1999 |
| WO | WO 2005/103300 | A2 | 11/2005 |

OTHER PUBLICATIONS

European Search Report dated May 10, 2010.

* cited by examiner

*Primary Examiner* — Jyoti Nagpaul
(74) *Attorney, Agent, or Firm* — Sughrue Mion, PLLC

(57) ABSTRACT

A diagnosis assisting system comprising: an analyzing section for analyzing a sample collected from a subject; a determining section for determining whether there is a possibility that a subject has a predetermined disease based on an analysis result obtained by the analyzing section; a notification section for notifying the possibility when the determining section has determined that there is the possibility; and a diagnosis assisting information display section for displaying a diagnosis assisting information screen which displays diagnosis assisting information related to the predetermined disease, is disclosed. A diagnosis assisting information providing device and a computer program product are also disclosed.

14 Claims, 30 Drawing Sheets

Case I.A.1 : Microangiopathic haemolytic anaemia (MAHA)

*Example case*

Summary

In case of ...
- Low platelet count / thrombocytopenia
- Otherwise inconspicuous CBC
- High immature platelet fraction IPF%
- Elevated reticulocytes
- Elevated fragmentocytes

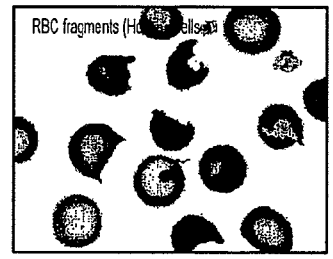

It is important to consider:
Is a plasma exchange or platelet transfusion necessary?
Can MAHA be excluded?

Background:
The measurement of IPF (→) helps to quickly identify the cause of thrombocytopenia. If thrombocytopenia is due to increased platelet consumption or destruction IPF is elevated. In case of decreased platelet production by the bone marrow IPF is not elevated. Reticulocytes and fragments (→) indicates the RBC destruction due to intravascular PLT consumption (Thrombosis).

FIG. 18

Example
*Example case*

**\*Case History:**
A 45 year old female presents at the hospital's emergency department with symptoms of back pain and fever (38,4°C).

**\*The diagnostic situation:**
Single striking haematology result of 22,000 platelets/µL without visible bruises or bleeding. Remaining blood count and clinical chemical profile inconspicuous, except CRP (25 mg/L) and LDH (480 U/L).

-->Is an immediate intervention required, i.e. platelet transfusion? Or is there time to wait until next morning to further investigate the cause of the thrombocytopenia?

**\*The challenge:**
Several types of isolated thrombocytopenia require immediate intervention. Thrombotic thrombocytopenic purpura (TTP) is one of them, requiring prompt plasma exchange to save the patient's life. However, typical clinical symptoms (neurological abnormalities, fever, renal failure) are not always present. How to confirm or exclude TTP?

Patient results shows, an isolated thrombocytopenia with platelet production bone marrow response, indicated by increase immature thrombocytes fraction (IPF %) and a compensated reticulocytosis with an increase of erythrocytes destruction, indicate by increase RBC fragments.
Fragmentocytes in peripheral blood are typical of microangiopathic haemolytic anaemiae (MAHA) such as TTP. However, they are hard to be identified by untrained personnel, i.e. during nightshifts. Often signs of haemolysis may be present (elevated unconjugated bilirubin and LDH), but they are non-specific.

The solution:
The laboratory determines from the same blood sample that is used for the normal blood count fragmentocytes, reticulocytes (RET) and immature platelets (IPF) fully automated within less than a minute. In case all three parameters are markedly increased the patient suffers most likely from MAHA and requires the respective treatment. If they are normal a MAHA (i.e. TTP) can be almost excluded.

**\*The results:**
The patient had 12% IPF, 115,000 reticulocytes / µL and 0.7% fragmentocytes (all elevated). This was highly indicative of MAHA. The elevated LDH supported this suspicion. The platelets were further falling to 12,000 µ/L within 3 hours. At this stage the decision for a plasma exchange was taken. The condition of the patient stabilised over time.

**\*The outcome:**
A plasma sample taken before the plasma exchange was sent to a specialised laboratory where the activity of ADAMTS13 was determined. It was only 8% of the normal concentration. This confirmed the diagnosis of TTP. Over a period of 5 months the patient suffered repeated episodes of thrombocytopenia.

FIG.19

Lab result
*From the laboratory*

The patient had 12% IPF, 115,000 reticulocytes / μL and 0.7% fragmentocytes, all elevated. This was highly indicative of MAHA. The elevated LDH supported this suspicion. The platelets were further falling to 12,000 μ/L within 3 hours.

The PLT-I Histogram (2b) of the automated analyser indicates an abnormal distribution caused by the combination of elevated numbers of immature platelets (2a) and fragmentocytes in the patients' blood. A closer look at the PLT-fluorescence channel shows a striking result for the IPF parameter (2c) which is not as prominent in healthy patients (2d)

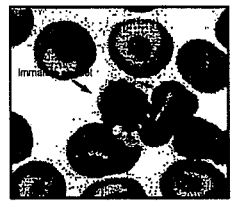

2A) Immature platelets in blood smear

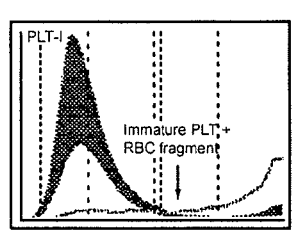 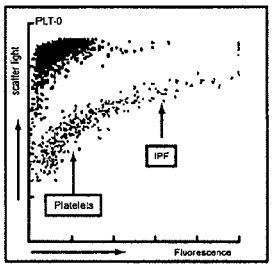 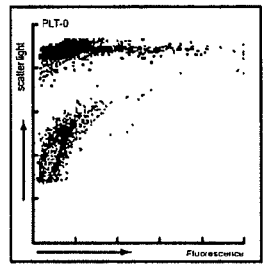

2b) PLT abnormal        2c) Patient's IPF        2d) Healthy individual's IPF

From the scattergram of the optical RBC channel (3b) one can clearly see the presence of fragmentocytes, normally identified microscopically on a blood smear (3a). A scattergram from a normal patient (3c) does not show any fragmentocytes.

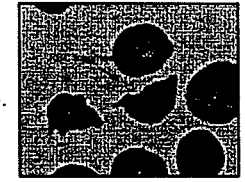

3a) Fragmentocytes in blood smear

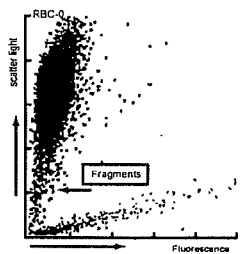 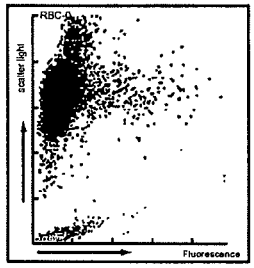

3b) Patient's RBC scattergram       3c) Healthy individual's RBC

FIG. 20

Underlying disease
*Microangiopathic hemolytic anemia (MAHA)*

Microangiopathic hemolytic anemia (MAHA) is a subgroup of hemolytic anemia caused by factors in the small blood vessels. In diseases such as hemolytic uremic syndrome (HUS), disseminated intravascular coagulation (DIC), thrombotic thrombocytopenic purpura (TTP), as well as malignant hypertension (Preeclampsia / HELLP), the endothelial layer of small vessels are damaged with resulting fibrin deposition and platelet aggregation. As red blood cells travel through these damaged vessels, they are shredded. The result is red cell fragmentation and intravascular hemolysis. Under the microscope, damaged red cells have the appearance of schistocytes. The most important causes are:

- Thrombotic thrombocytopenic purpura (TTP)
- Hemolytic uremic syndrome (HUS)
- Disseminated intravascular coagulation (DIC)
- HELLP syndrome and eclampsia
- Several other rare causes In all causes, the mechanism of MAHA is the formation of a fibrin mesh due to increased activity of the system of coagulation. The red blood cells are physically cut by these protein networks, and the fragments are identical to the schistocytes.

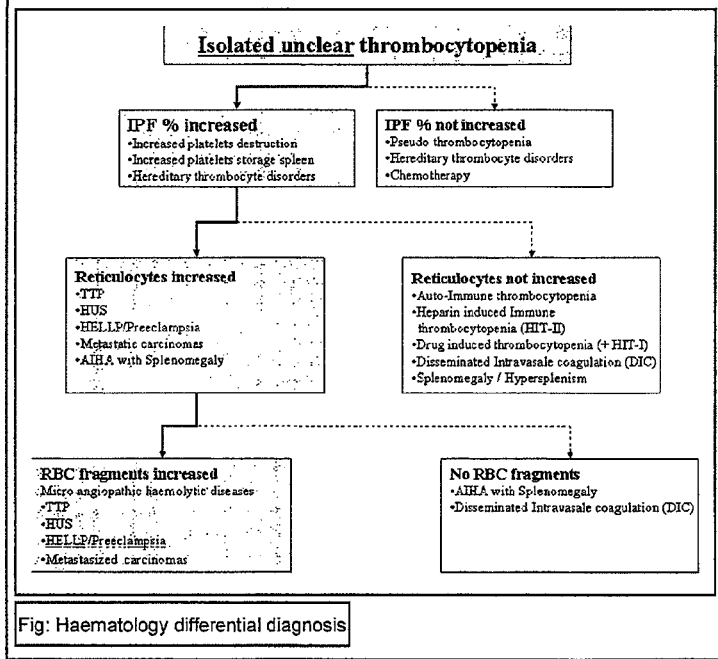

Fig: Haematology differential diagnosis

FIG. 21

*Underlying disease*
*Thrombotic thrombocytopenic Purpura*
*(TTP, Moschcowitz Disease)*

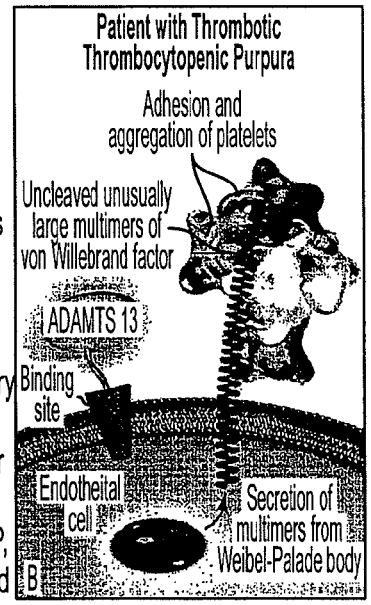

Patient with Thrombotic Thrombocytopenic Purpura

*Thrombotic thrombocytopenic Purpura exists in three forms: Idiopathic, secondary and the inherited form Upshaw-Shulman syndrome. Patients show spontaneous aggregations of platelets and activation of coagulation. This leads to clotting and haemolysis in small blood vessels with end-organ damage like kidney failure as the worst possible consequence. In most cases of the disease the cause is a lack or deficiency of the enzyme ADAMTS13. In idiopathic TTP the ADAMTS 13 deficiency is mainly linked to auto-antibodies while in US syndrome the cause is hereditary. 40% of all cases of TTP are the so called secondary form, where patients usually show predisposing factors like cancer, bone marrow transplantation, pregnancy, HIV infection or it can be due to some medications. The ADAMTS13 activity in secondary TTP is not as severely depressed as in idiopathic TTP, but inhibitors cannot be found. Mortality rate is 95% for untreated cases, but with early diagnosis the outcome is reasonable favourable at 80-90% survival under plasmapheresis. 1/3 of patients relapse within 10 years. Secondary TTP has the worst prognosis with mortality rates of 59-100%. Diagnosis is made on basis of symptoms and blood tests, e.g. through typical <<helmet cells>> on bloodfilm, thrombocytopenia, haemolytic anaemia, reticulocytes, fragmentocytes, LDH. Other thrombocytopenic conditions must be excluded.*
Treatment:
Plasma exchange specifically for TTP For view see:
n Moake JL. Thrombotic microangiopathies.
N Engl J Med 2003;347:589-600. PMID 12192020.
n Moake JL. Von Willebrand factor, ADAMTS-13, and thrombotic thrombocytopenic purpura.
Semin Hematol 2004;41:4-14. PMID 14727254

FIG. 22

Explanation
*Immature platelets fraction (IPF)*

In 1969 Ingram and Coopersmith observed newly released platelets that could be stained with new methylene blue and recognized by light microscopy.
It was later found out that they contain RNA and they were suggested to be the platelet analogue of the red blood cell precursor reticulocyte, therefore they were first named, reticulated platelets'The number of reticulated platelets reflects the rate of thrombopoiesis, increasing when platelet production rises and decreasing when production falls. Estimation was made possible by the means of Flow cytometry and with the Sysmex XE analysers.

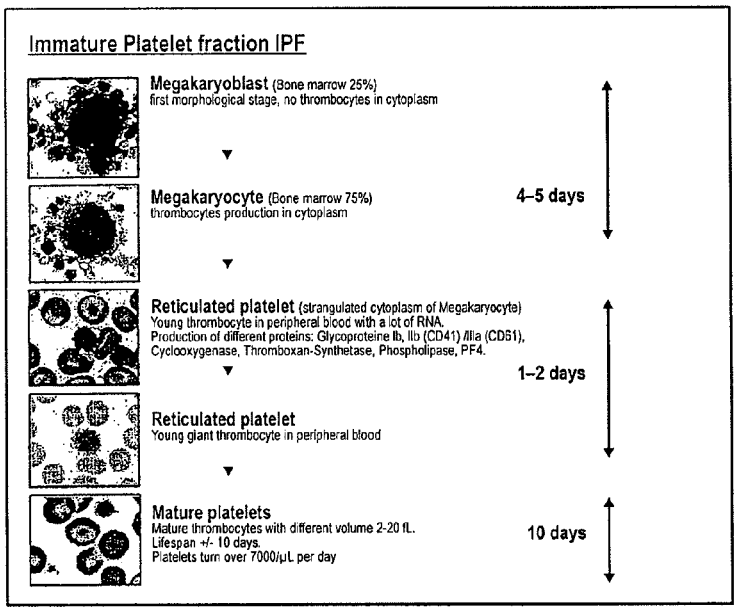

Fig 3. Thrombopoiesis

FIG. 23

Additional Information
Literature

Literature immature platelets (IPF):

1. Ingram, M. and Coopersmith, A. (1969) Reticulated Platelets following Acute Blood Loss, British Journal of Haematology; 17:225-229.

2. Kienast, J. & Schmitz, G. (1990) Flow cytometric analysis of thiazole orange uptake by platelets: a diagnostic aid in the evaluation of thrombocytopenic disorders, Blood: 75:116–121

3. Watanabe-K Takeuchi, K., Kawai, Y., Ikeda, Y., Kubota, F., Nakamoto, H (1995) Automated measurement of reticulated platelets in estimating thrombopoiesis, European Journal of Haematology; 54:163-171

4. Briggs C, Kunka S, Hart D, Oguni S, Machin S, : *Assessment of an immature platelet fraction (IPF) in peripheral thrombocytopenia.* Brit J Haematol 2004; 126: 93

5. Briggs C, Hart D, Kunka S, Oguni S, Machin S, 2006: *Immature platelet fraction measurement: a future guide to platelet transfusion requirement after haematopoietic stem cell transplantation.* Transfusion Medicine 16: 101

6. Kickler T, Oguni S, Borowitz M, 2006: A clinical evaluation of high fluorescent platelet fraction percentage in thrombocytopenia. Am J Clin Pathol 125:282

Literature Platelets general:

1. Norfolk, DR, Ancliffe, PJ, Contreras, M, Hunt, BJ, Machin, SJ, Murphy, WG. & Williamson, LM. (1997) Consensus Conference on Platelet Transfusion, Royal College of Physicians of Edinburgh 27–28 November. British Journal of Haematology; 101:609–617.

2. Ancliff, P.J. & Machin, S.J. (1998) Trigger factors for the prophylactic platelet transfusion. Blood Reviews, 12, 234–238.

Literature Fragments (FRC):

1. Jiang (2001) Fragments, Clin Lab Haem 2001

2. Saigo. (2002) Fragments in TTP, Clin Lab Haem 2002

3. S. Imoto (2005) Fragments, *Lab Hematol.* 2005;11:131-136

FIG.24

Case I.A.2:   HELLP- Syndrome
(Haemolysis with elevated liver enzyme concentration in serum of low platelets counts)

*Example case*

Summary

In case of ...
- Thrombocytopenia in pregnant woman
- High immature platelet fraction IPF%
- Elevated reticulocytes

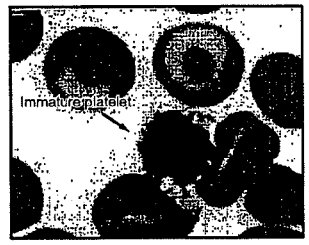

It is important to consider:
A HELLP syndrome can cause a serious threat to the mother's life and fetal death is also often seen in severe cases.
A quick diagnosis is therefore required.

Background:
The measurement of IPF (→) helps to quickly identify the cause of thrombocytopenia. If thrombocytopenia is due to increased platelet consumption or destruction IPF is elevated. In case of decreased platelet production by the bone marrow IPF is not elevated. The increased reticulocyte count indicates a stimulated erythropoiesis due to RBC destruction.

FIG. 25

*Example*

Example case

**\*Case History:**

A 27 year old 29 weeks pregnant women presents at antenatal care unit with pregnancy induced preeclampsia symptoms, high blood pressure, edema of the face and hands.

**\*The diagnostic situation:**

Haematology result of 10.3 g/dl (6.4 mmol/L) haemoglobin and 65.000 platelets /µL, and conspicuous increase compensated reticulocyte count.

→ A HELLP syndrome can cause a serious threat to the mother's life and fetal death. Is an immediate intervention the delivery of the baby required, or can we wait?

**\*The challenge:**

Preeclampsia can causes malfunction of some maternal organs, such as kidneys, liver and the blood vessels. The complications of pre-eclampsia are often more pronounced than in pregnancy induced hypertension, but often not worse than in HELLP syndrome. A HELLP syndrome can cause a serious threat to the mother's life and fetal death is also often seen in severe cases. A quick diagnosis is therefore required.

**\*The solution:**

The laboratory determines from the same blood sample that is used for the normal blood count reticulocytes (RET) and immature platelets (IPF) fully automated within less than a minute.

**\*The results:**

The patient had 14,4% IPF, 135,000 reticulocytes / µL, 17,7% IRF and RPI of 2.1 (all elevated). This was highly indicative of MAHA. The elevated LDH, fibrin degradation products (FDPs) and Proteinuria supported this suspicion and diagnosis of HELLP syndrome.

**\*The outcome:**

Due to the mild anemia, the patient was treated corticosteroids and antihypertensives and the DIC was treated with fresh frozen plasma to replenish the coagulation proteins. 5 days later a caesarean section (child birth) where required.

FIG.26

Lab result
*From the laboratory*

The patient showed a thrombocytopenia of 65.000/μL and 14.4% IPF, a reticulocyte count of 135.000/μL and 17.7% IRF (RPI 2.1), all elevated. This was highly indicative of MAHA. The elevated LDH, fibrin degradation products (FDPs), hypertension and proteinuria supported this suspicion and diagnosis of HELLP syndrome.

The PLT-fluorescence channel of the automated analyser shows a striking result for the IPF parameter (2a) which is not as prominent in healthy patients (2b), due to the immature platelets as shown in the blood film (2c)

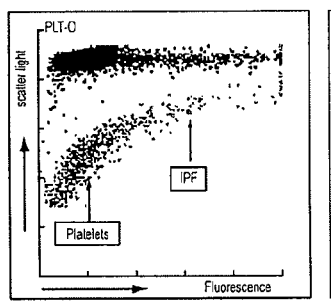 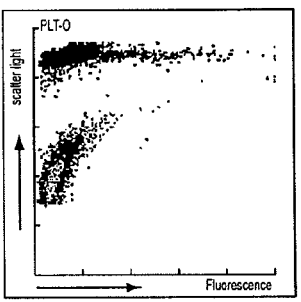 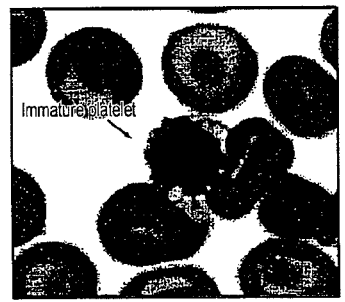

2a) Patient's IPF scattergram  
2b) Healthy individual's IPF scattergram  
2c) Immature platelet in blood From the scattergram of the optional RBC channel (3a) there is clearly seen the increase reticulocytes and immature reticulocyte fraction (IRF). A scattergram from a normal patient (3b) show lower values.

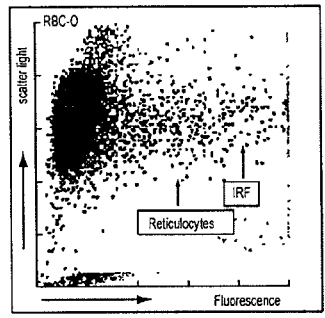 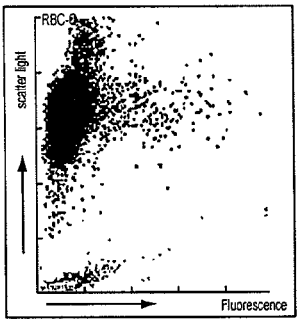

3a) Patient's RBC scattergram  
3b) Healthy individual's RBC scattergram

FIG. 27

DIAGNOSIS ASSISTING SYSTEM, DIAGNOSIS ASSISTING INFORMATION PROVIDING DEVICE AND COMPUTER PROGRAM PRODUCT

FIELD OF THE INVENTION

The present invention relates to a diagnosis assisting system, a diagnosis assisting information providing device and a computer program product.

BACKGROUND

Physicians often refer to data obtained from blood analysis, urine analysis and the like when diagnosing the condition of a patient. Such blood analysis and urine analysis involves the use of blood cell counters which count and classify blood cells contained in blood samples, blood coagulation measuring apparatuses which analyze blood coagulation function, immunoanalyzers which analyze cancer morbidity and the presence of hepatitis virus and the like using an antigen-antibody reaction, biochemical analyzers which chemically analyze proteins, and urine analyzers which analyze urine composition.

There are various types of such examinations, and various data items are included in the examination data. Moreover, since a single ailment can influence the examination data of various items, the physician must be cognizant of the influences on the form of items (for example, high and low values diverging from the normal value range of healthy individuals) caused by an ailment when specifically considering that particular ailment. The physician thus bears a considerable burden in confirming the possibility of an ailment when using such examination data in the diagnosis. Japanese Laid-Open Patent Publication No. 11-326315 discloses a method of judging a type of anemia, the ailment of β-thalassemia, with a high degree of sensitivity based on analysis results. Such judging results may assist in the diagnosis if provided to the physician together with the examination data. Japanese Laid-Open Patent Publication No. 7-57018 discloses a comprehensive medical diagnosis assisting apparatus which specifies an ailment name by fuzzy logic using a plurality of clinical examination data output from an automated biochemical analyzer, and displays the specified ailment name.

The apparatus disclosed in Japanese Laid-Open Patent Publication No. 7-57018 only displays the specified ailment name and ailment region, however, and is not configured to further display information referenced in making the diagnosis, such as characteristics of the ailment and cited literature. The physician must therefore personally seek further information when considering the diagnosis of the ailment.

SUMMARY OF THE INVENTION

The scope of the present invention is defined solely by the appended claims, and is not affected to any degree by the statements within this summary.

A first aspect of the present invention is a diagnosis assisting system comprising: an analyzing section for analyzing a sample collected from a subject; a determining section for determining whether there is a possibility that a subject has a predetermined disease based on an analysis result obtained by the analyzing section; a notification section for notifying the possibility when the determining section has determined that there is the possibility; and a diagnosis assisting information display section for displaying a diagnosis assisting information screen which displays diagnosis assisting information related to the predetermined disease.

A second aspect of the present invention is a diagnosis assisting information providing device comprising: an obtaining section for obtaining an analysis result of a sample collected from a subject; a determining section for determining whether there is a possibility that a subject has a predetermined disease based on the analysis result obtained by the obtaining section; a notification section for notifying the possibility when the determining section has determined that there is the possibility; and a diagnosis assisting information display section for displaying a diagnosis assisting information screen which displays diagnosis assisting information related to the predetermined disease.

A third aspect of the present invention is a computer program product, comprising: a computer readable medium; and instructions, on the computer readable medium, adapted to enable a general purpose computer to perform operations, comprising: obtaining an analysis result of a sample collected from a subject; determining whether there is a possibility that a subject has a predetermined disease; notifying the possibility when it has been determined that there is the possibility; and displaying a diagnosis assisting information screen which displays diagnosis assisting information related to the predetermined disease.

BRIEF DESCRIPTION OF THE DRAWINGS

FIG. 18 shows the diagnosis assisting information display region when the "summary" tab has been selected for "MAHA";

FIG. 19 shows the diagnosis assisting information display region when the "example case" tab has been selected for "MAHA";

FIG. 20 shows the diagnosis assisting information display region when the "lab result" tab has been selected for "MAHA";

FIG. 21 shows the diagnosis assisting information display region when the "underlying disease" tab has been selected for "MAHA";

FIG. 22 shows the diagnosis assisting information display region when the "TTP" tab has been selected for "MAHA";

FIG. 23 shows the diagnosis assisting information display region when the "IPF" tab has been selected for "MAHA";

FIG. 24 shows the diagnosis assisting information display region when the "additional information" tab has been selected for "MAHA";

FIG. 25 shows the diagnosis assisting information display region when the "summary" tab has been selected for "HELLP-syndrom";

FIG. 26 shows the diagnosis assisting information display region when the "example case" tab has been selected for "HELLP-syndrom";

FIG. 27 shows the diagnosis assisting information display region when the "lab result" tab has been selected for "HELLP-syndrom";

DETAILED DESCRIPTION OF THE PREFERRED EMBODIMENTS

The preferred embodiments of the present invention will be described hereinafter with reference to the drawings.

Figure 1:
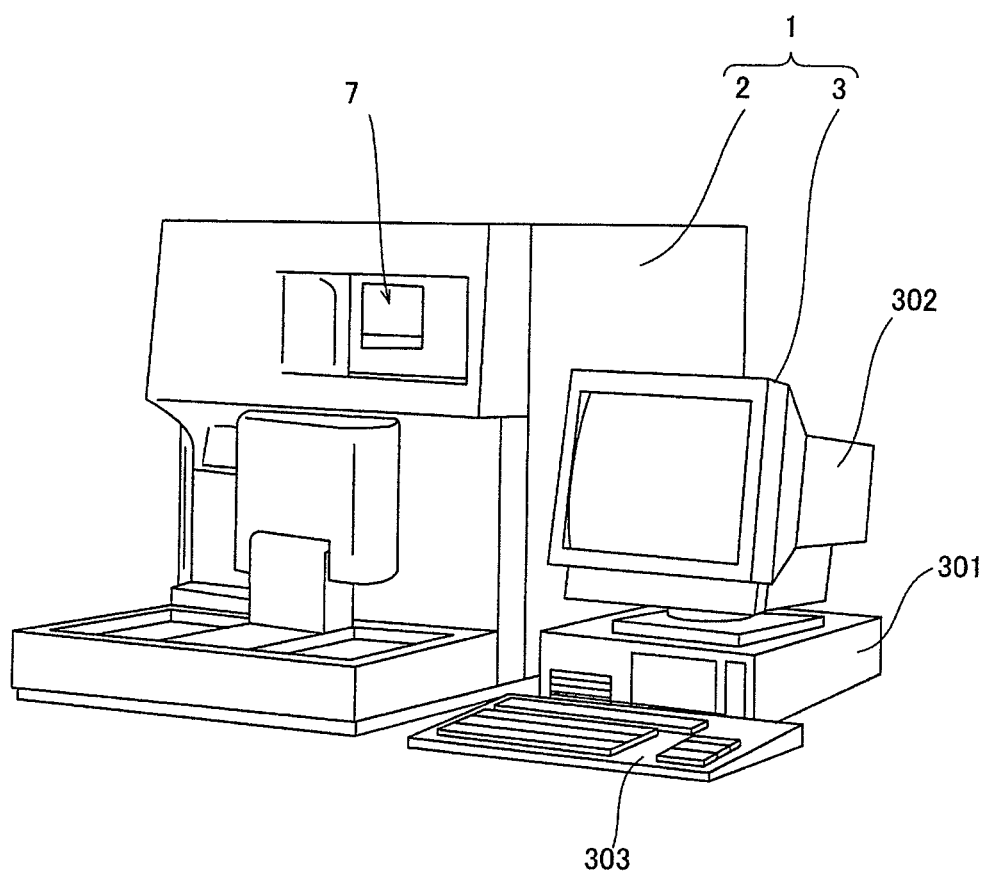
FIG. 1 is a perspective view showing an overview of a blood analyzer applied to the diagnosis assisting system of an embodiment of the present invention.
Figure 2:
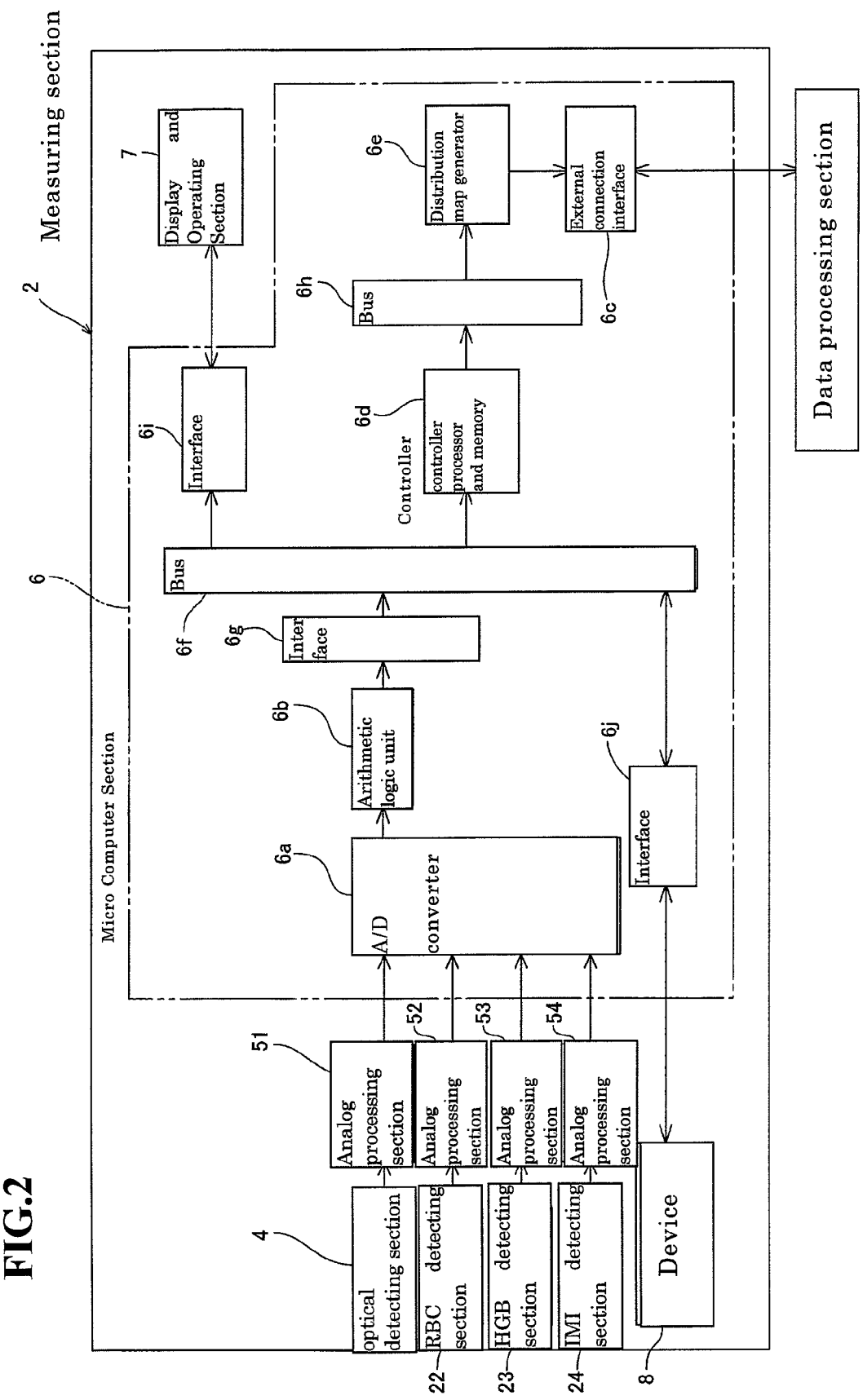
FIG. 2 is a block diagram showing the measuring section of the blood analyzer of FIG. 1.

FIG. 1 is a perspective view showing an overview of a blood analyzer applied to the diagnosis assisting system of an embodiment of the present invention. FIG. 2 is a block diagram showing the structures of the measuring section and the data processing section of the blood analyzer of FIG. 1. FIGS. 3 through 14 illustrate the structure of the blood analyzer of FIG. 1. The general structure of the blood analyzer 1 is first described as a diagnosis assisting system of an embodiment of the present invention with reference to FIGS. 1 through 14.

The blood analyzer 1 is an apparatus which analyzes the blood cells in blood by irradiating laser light on the individual particles, such as cells and blood cells, that pass through a flow cell, and detects the scattered light and the fluorescent light from the individual particles.

The blood analyzer 1 is configured by a measuring section 2 which has the function of measuring blood samples, and a data processing section 3 which analyzes the measurement results output from the measuring section 2 to obtain an analysis result, as shown in FIG. 1. The measuring section 2 is provided with an optical detecting section 4, an RBC detecting section 22, an HGB detecting section 23, an IMI detecting section 24, analog processing sections 51 through 54 which process the outputs from the respective detecting sections 4, 22, 23, and 24, a microcomputer 6, a display and operating section 7, and a device 8 for blood measurements as shown in FIG. 2.

Figure 3:
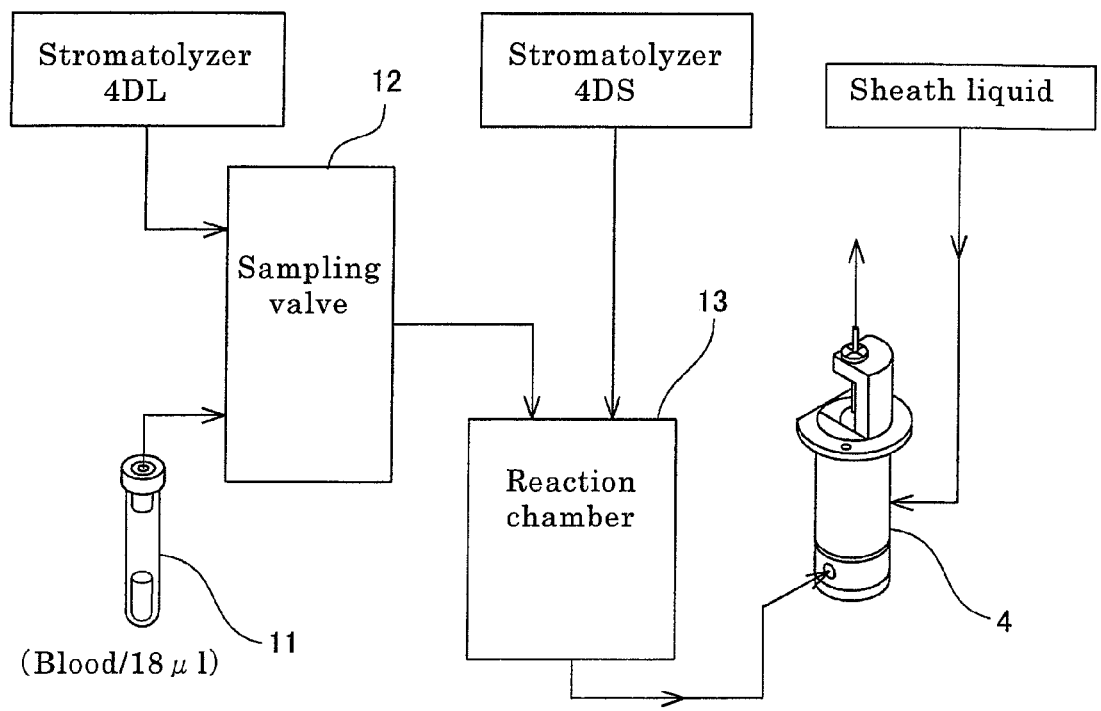
FIG. 3 illustrates the configuration when the blood analyzer of FIG. 1 performs the 4DIFF measurement.

As shown in FIG. 3, the measuring section 2 is provided with a reaction chamber 13 and a sampling valve 12 which allocates a fixed amount of blood sample aspirated from a collection tube 11 that contains a fixed amount of blood sample. The sampling valve 12 is configured to allocate the blood sample of the collection tube 11, which has been aspirated by an aspirating pipette that is not shown in the drawing, into an aliquot of 18 µL as a measurement sample for classifying four types of white blood cells, an aliquot of 18 µL as a measurement sample for a white blood cell count and basophil measurement, an aliquot of 4 µL as a measurement sample for red blood cells and platelets (RBC/PLT), an aliquot of 3 µL as a hemoglobin (HGB) measurement sample, and an aliquot of 2.4 µL as an immature erythrocyte (IMI) measurement sample. The sampling valve 12 is further configured to be capable of mixing predetermined hemolytic agent (Stromatolyzer 4DL, a product of Sysmex Corporation) with the measurement sample for classifying four types of white blood cells. That is, the sampling valve 12 can generate samples which contain a mixture of hemolytic agent used to measure four classifications of white blood cells in and a predetermined amount of a blood sample used to measure four classifications of white blood cells. The reaction chamber 13 is connected to the sampling valve 12, and is configured to further mix a staining reagent (Stromatolyzer 4DS, a product of Sysmex Corporation) used for white blood cell measurement with the sample generated in the sampling valve 12 so as to induce a reaction for a predetermined time (22 seconds) to prepare a white blood cell four-classification measurement sample (4DIFF measurement sample). The reaction chamber 13 is also connected to the optical detecting section 4, and is configured to have the 4DIFF measurement sample prepared in the reaction chamber 13 flow into the optical detecting section 4. The optical detecting section 4 performs the measurements to classify the four types of white blood cells using flow cytometry which is described later.

Figure 4:
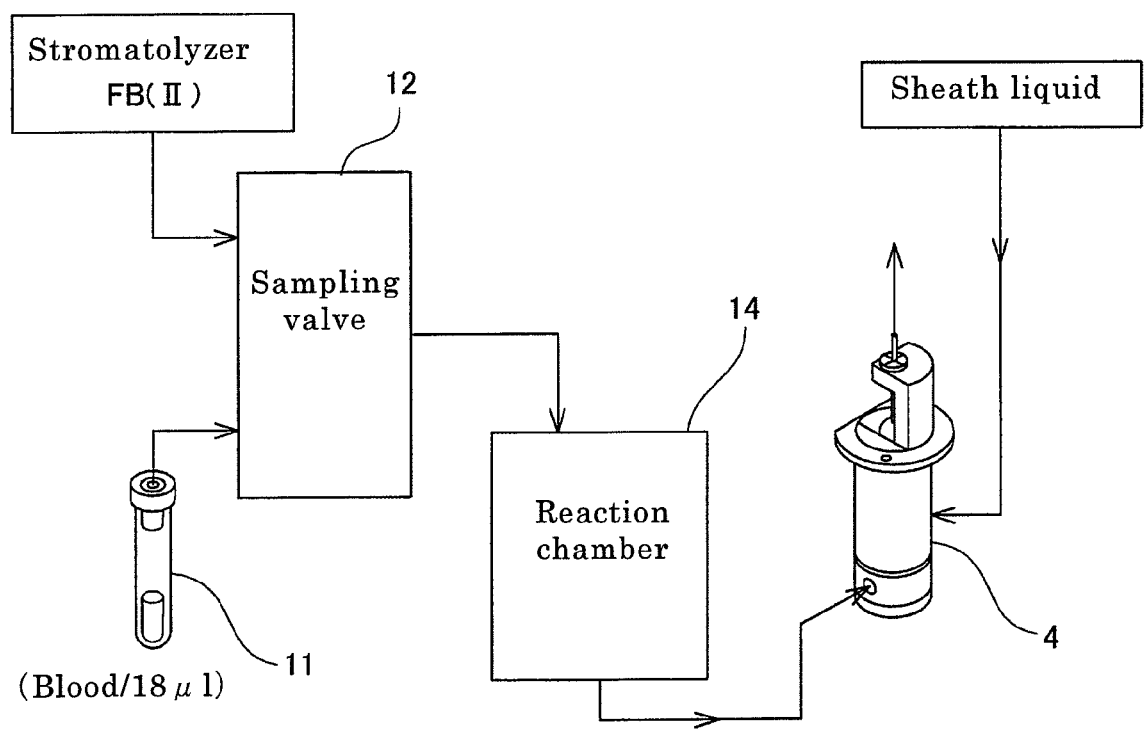
FIG. 4 illustrates the configuration when the blood analyzer of FIG. 1 performs the WBC/BASO measurement.

The sampling valve 12 is also configured to be capable of mixing a predetermined hemolytic agent (Stromatolyzer FB(II), a product of Sysmex Corporation) with the predetermined amount (18 µL) of blood sample for the white blood cell count and basophil measurement, as shown in FIG. 4. That is, the sampling valve 12 can generate a dilute sample for the white blood cell count and basophil measurement which contains a predetermined hemolytic agent mixed in a predetermined amount of blood sample. The reaction chamber 14 is connected to the sampling valve 12, and the dilute sample produced in the sampling valve 12 is held for a predetermined time (14 seconds) in the reaction chamber 14 to allow the reaction of the sample to dissolve the red blood cells in the sample. A WBC/BASO measurement sample is thus prepared. The WBC/BASO measurement sample prepared in the reaction chamber 14 is introduced to the optical detecting section 4, which measures the sample by flow cytometry in a manner to be described later.

Figure 5:
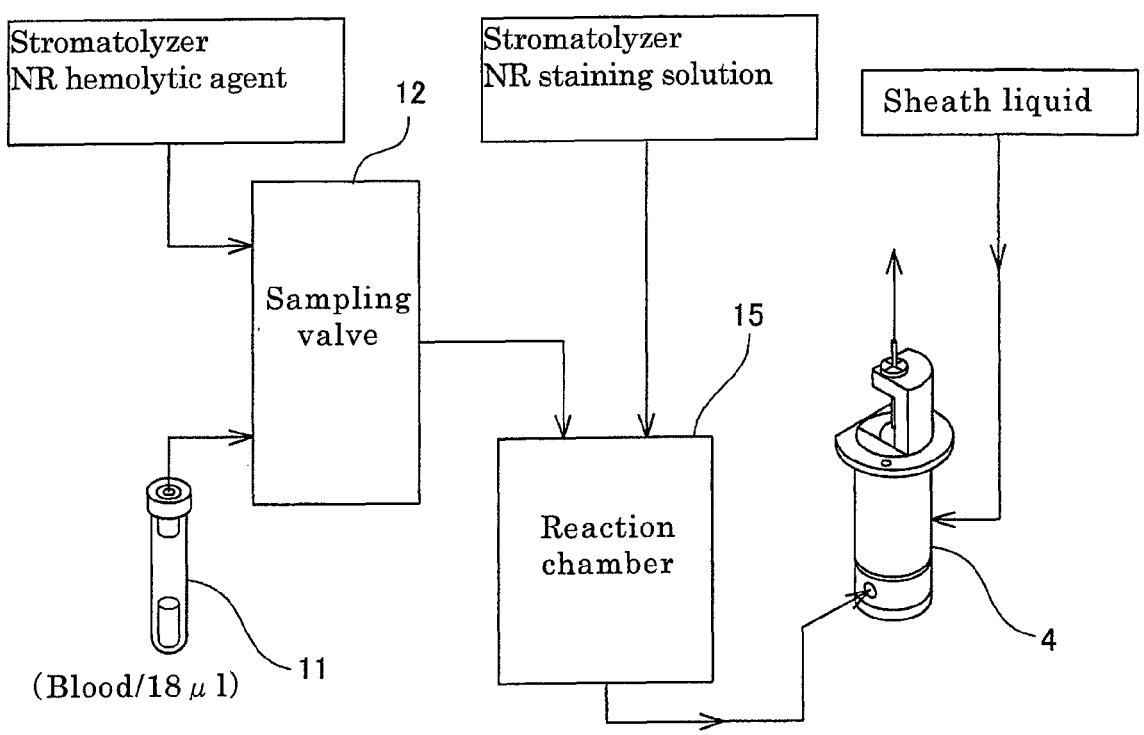
FIG. 5 illustrates the configuration when the blood analyzer of FIG. 1 performs the NRBC measurement.

The sampling valve 12 is also configured to be capable of mixing a predetermined hemolytic agent (Stromatolyzer NR hemolytic agent, a product of Sysmex Corporation) with the predetermined amount (18 µL) of blood sample for the nucleated red blood cell classification measurement, as shown in FIG. 5. The reaction chamber 15 is connected to the sampling valve 12, and is capable of further mixing a staining reagent (Stromatolyzer NR staining solution, a product of Sysmex Corporation) used for nucleated red blood cell classification measurement with the sample produced in the sampling valve 12, and allow the reaction of the mixture for a predetermined time (7 seconds) to prepare a nucleated red blood cell classification measurement sample (NRBC measurement sample).

The NRBC measurement sample prepared in the reaction chamber 15 is introduced to the optical detecting section 4, which measures the sample by flow cytometry in a manner to be described later.

Figure 6:
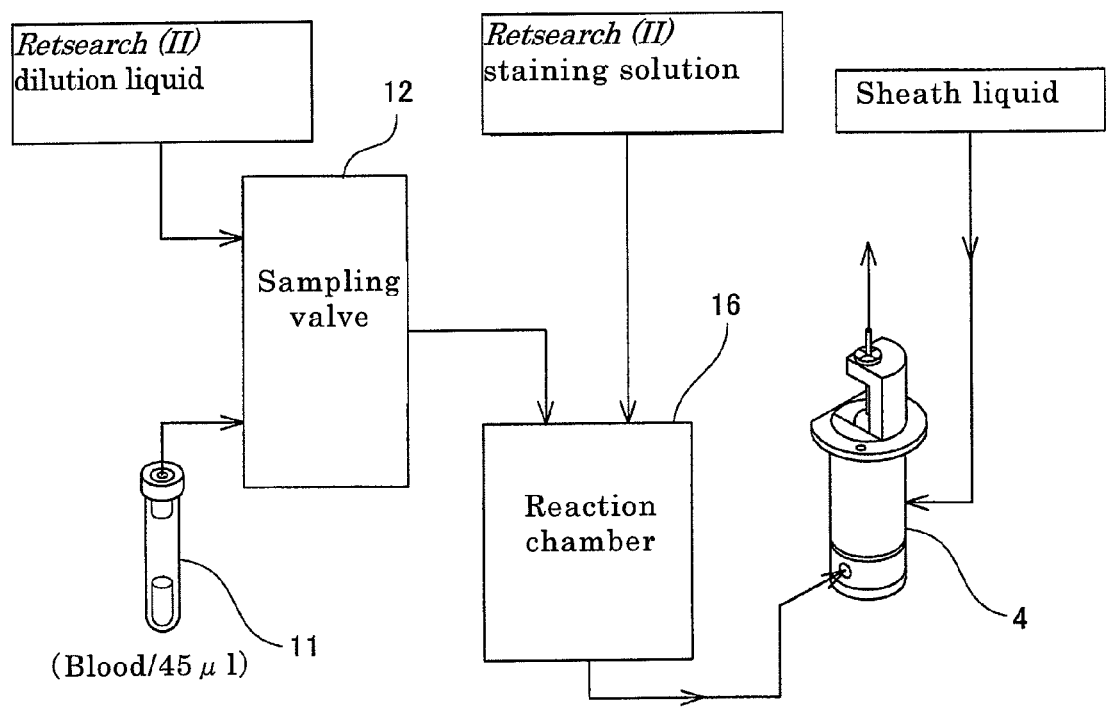
FIG. 6 illustrates the configuration when the blood analyzer of FIG. 1 performs the RET measurement.

As shown in FIG. 6, the sampling valve 12 is configured to mix a predetermined dilution liquid (Retsearch (II), a product of Sysmex Corporation) with a predetermined amount (4.5 µL) of a blood sample to classify and measure reticulocytes and platelet groups. The reaction chamber 16 is connected to the sampling valve 12, and is capable of further mixing a staining reagent (Retsearch (II) stain, a product of Sysmex Corporation) used for reticulocyte and platelet classification measurements with the sample produced in the sampling valve 12, and allow the reaction of the mixture for a predetermined time (31 seconds) to prepare a reticulocyte and platelet classification measurement sample (RET measurement sample). The RET measurement sample prepared in the reaction chamber 16 is introduced to the optical detecting section 4, which measures the sample by flow cytometry in a manner to be described later.

Figure 7:
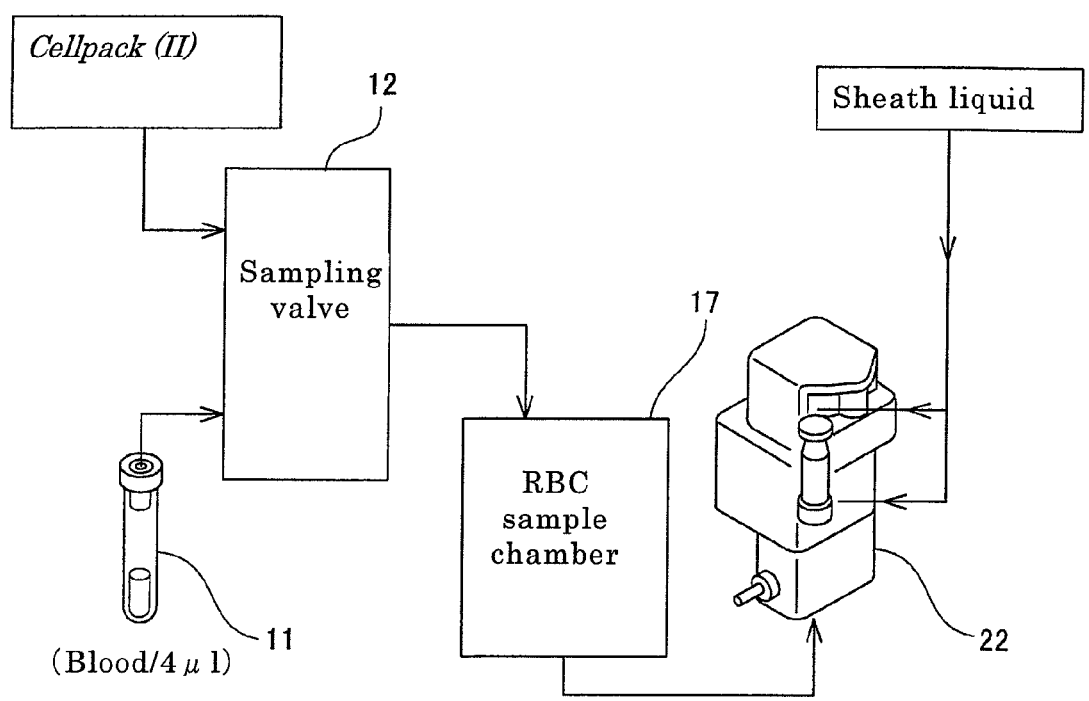
FIG. 7 illustrates the configuration when the blood analyzer of FIG. 1 performs the RBC measurement.

The sampling valve 12 is capable of mixing a predetermined dilution liquid (Cellpack(II), a product of Sysmex Corporation) with a fixed amount (4 µL) of blood sample used for red blood cell and platelet measurements, as shown in FIG. 7. That is, the sampling valve 12 can produce a dilute sample for red blood cell and platelet measurements which contains a predetermined reagent (dilution liquid) mixed with a fixed amount of blood sample. The RBC sample chamber 17 is connected to the sampling valve 12, and is configured to accommodate and mix the dilute sample (RBC measurement sample) produced in the sampling valve 12. The RBC sample chamber 17 is connected to the RBC detecting section 22, and is configured to have the RBC measurement sample flow into the RBC detecting section 22.

Figure 8:
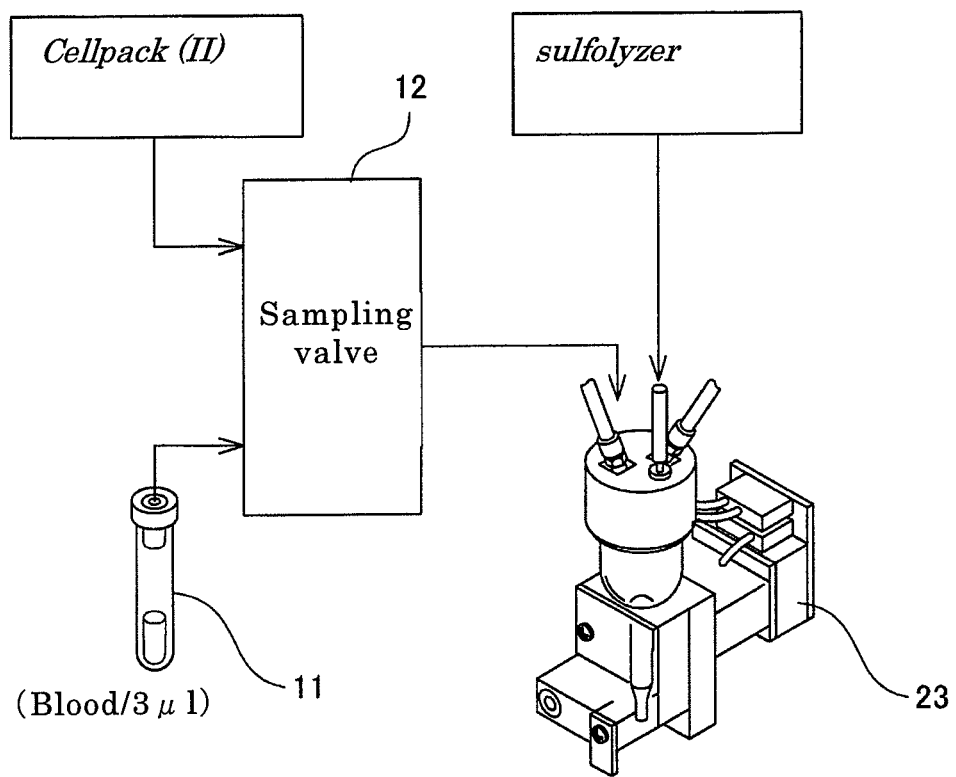
FIG. 8 illustrates the configuration when the blood analyzer of FIG. 1 performs the HGB measurement.

The sampling valve 12 is capable of mixing a predetermined dilution liquid (Cellpack(II), a product of Sysmex Corporation) with a fixed amount (3 µL) of blood sample used for hemoglobin measurements, as shown in FIG. 8. That is, the sampling valve 12 is capable of producing a dilute sample for hemoglobin measurement (hemoglobin measurement sample) which contains a mixture of a predetermined reagent (dilution liquid) and a fixed amount of blood sample. The sampling valve 12 is connected to the HGB detecting section 23, and is configured to have the HGB measurement sample flow into the HGB detecting section 23.

Figure 9:
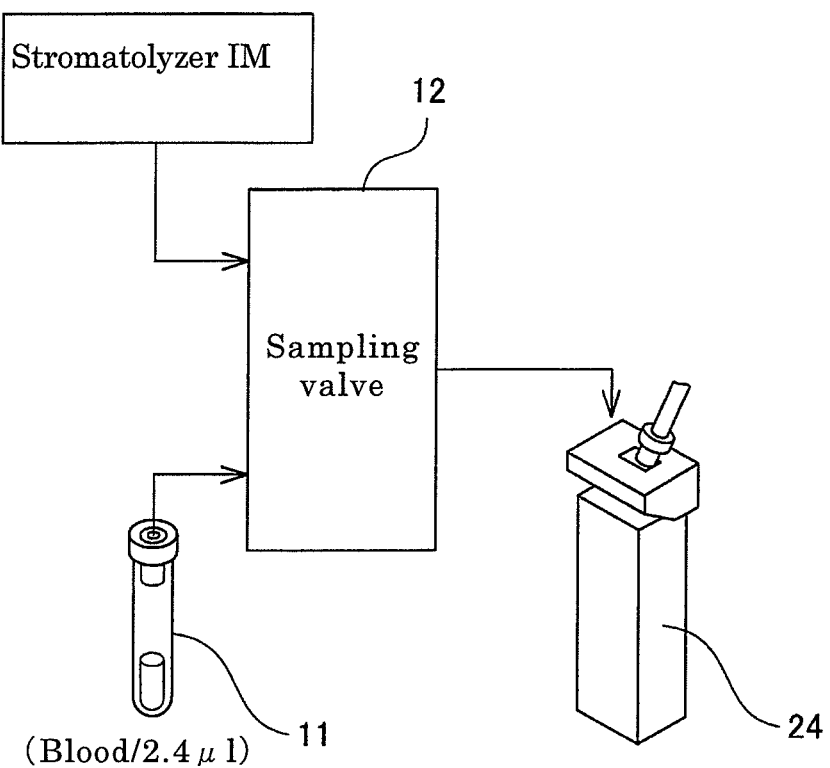
FIG. 9 illustrates the configuration when the blood analyzer of FIG. 1 performs the IMI measurement.

The sampling valve 12 is also capable of mixing a predetermined hemolytic agent (Stromatolyzer IM, a product of Sysmex Corporation) with a fixed amount (2.4 µL) of blood sample used for measuring immature erythrocytes, as shown in FIG. 9. That is, the sampling valve 12 is capable of producing a sample for measuring immature erythrocytes which contains a mixture of a predetermined reagent (hemolytic agent) and a fixed amount of blood sample. The IMI detecting section 24 is connected to the sampling valve 12, and is configured to have the sample (IMI measurement sample) produced in the sampling valve 12 flow into the IMI detecting section 24.

The optical detecting section 4 is configured to detect particles such as cells and blood cells within blood by flow cytometry. Flow cytometry is a method used to measure the chemical properties and physical properties of cells and other biochemical particles by having the cells and other biochemical particles pass through a narrow flow path. The optical detecting section 4 is configured to detect forward scattered light, side scattered light, and side fluorescent light emitted from the blood cells within a sheath flow cell 403 which has been irradiated by laser light to be described later. Scattered light is a phenomenon produced when the traveling light changes direction and is caused by the presence of particles such as blood cells in the direction of travel of the light which act as obstacles. Information related to the size and quality of the particles can be obtained by detecting the scattered light. Specifically, information related to the size of the particle (blood cell) can be obtained by detecting the forward scattered light, and information concerning the interior part of the particle can be obtained by detecting the side scattered light. The side fluorescent light is a phenomenon produced by the light emitted from a stained blood cell when the blood cell, which has been stained with a fluorescent substance, is irradiated by laser light. Information related to the degree to which the blood cell is stained can be obtained by detecting the side fluorescent light.

Figure 10:
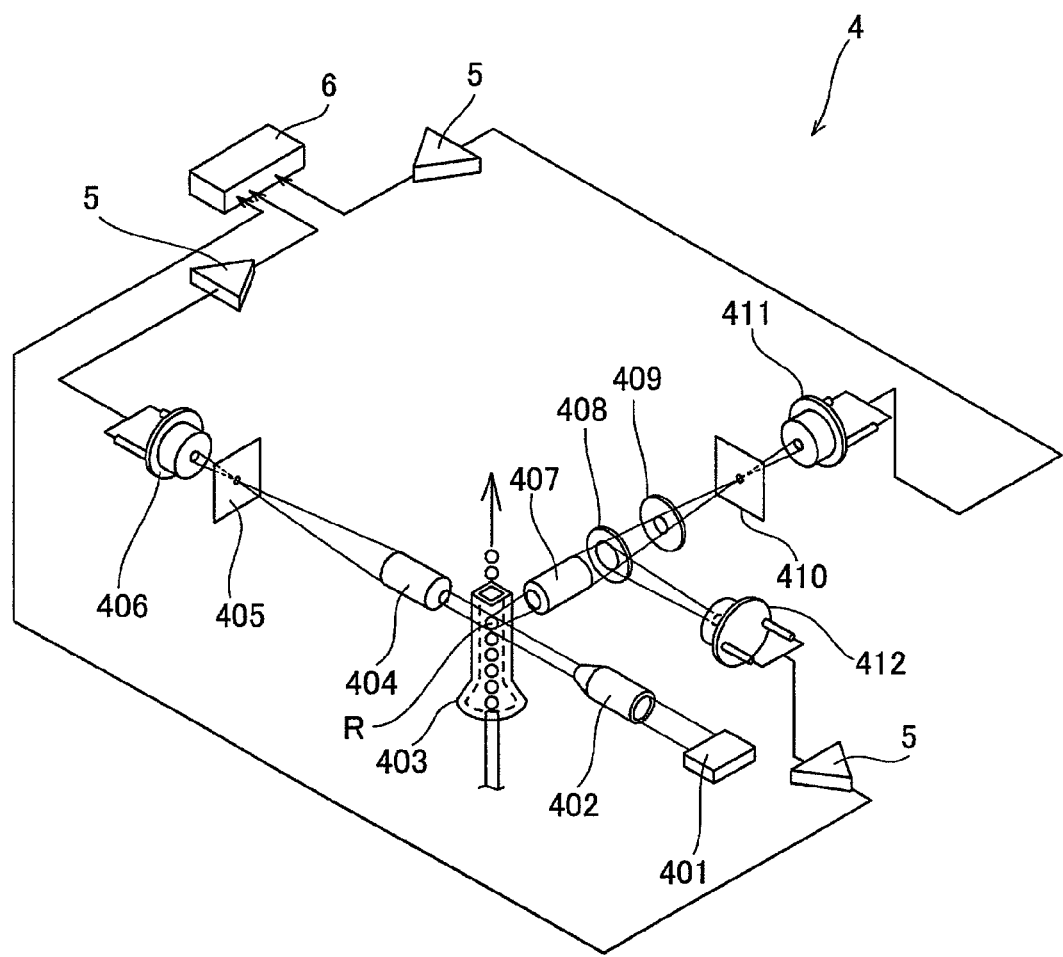
FIG. 10 illustrates the detecting section and the analog processing section of the blood analyzer of FIG. 1.

As shown in FIG. 10, the optical unit 4 includes a laser diode 401 which emits a laser beam, an irradiation lens unit 402, a sheath flow cell 403 through which the laser beam passes, a collective lens 404 which is disposed on a line extending from the laser diode 401 in the direction of travel of the emitted laser beam, a pinhole 405 and a photodiode 406, a collective lens 407 which is disposed in a direction that intersects the direction of travel of the laser beam emitted from the laser diode 401, a dichroic mirror 408, an optical filter 409, a pinhole 410 and a photodiode 411, and a photodiode 412 which is disposed on the side of the dichroic mirror 408.

The laser diode 401 is provided to emit light that irradiates the blood cells passing through the sheath flow cell 403. The irradiation lens unit 402 is configured to receive the light emitted by the laser diode 401 and irradiate the sheath flow cell 403. The light emitted from the laser diode 401 therefore irradiates the blood cells as the pass through the interior part of the sheath flow cell 403. Forward scattered light, side scattered light, and side fluorescent light then emanate from the blood cells. The forward scattered light emanates so as to travel on the line extending in the direction of travel of the light emitted from the laser diode 401. The collective lens 404 and the pinhole 405, which are disposed in the direction of travel of this forward scattered light, have the functions of collecting the forward scattered light and adjusting the focal point of the forward scattered light. The photodiode 406 is provided to receive the forward scattered light which has been focally adjusted by the collective lens 404 and the pinhole 405.

The side scattered light emanates in a direction which intersects the direction of travel of the light emitted from the laser diode 401. The collective lens 407 is provided to collect the side scattered light and is therefore disposed in the direction of travel of the side scattered light. The dichroic mirror 408 is also configured to have the side scattered light travel in the direction of the optical filter 409 by allowing the side scattered light collected by the collective lens 407 to pass therethrough. The optical filter 409 and the pinhole 410 have the function of adjusting the focal point of the side scattered light. The photodiode 411 is also provided to receive the side scattered light which has been focally adjusted by the pinhole 410.

The side fluorescent light emanates in a direction which intersects the direction of travel of the light emitted from the laser diode 401. The collective lens 407, which is disposed in the direction of travel of the side fluorescent light, has the functions of collecting both the side scattered light and the side fluorescent light. The dichroic mirror 408 is configured to reflect the side fluorescent light which has been collected by the collective lens 407, unlike the side scattered light which passes therethrough, so that the side fluorescent light is caused to travel to the photodiode 412. The photodiode 412 is provided to receive the side fluorescent light which has been reflected by the dichroic mirror 408.

The photodiode 406, the photodiode 411, and the photodiode 412 also have the function of converting the received light signals into electrical signals. As shown in FIG. 2, the optical detecting section 4 is provided to transmit the electrical signals which have been converted from the light signals to an analog processing section 5 via the photodiode 406 (refer to FIG. 10), the photodiode 411 (refer to FIG. 10), and the photodiode 412 (refer to FIG. 10).

The analog processing section 5 is connected to perform amplification and waveform processing of the input electrical signals, and to transmit the electrical signals (waveform signals) to a microcomputer 6.

Figure 11:
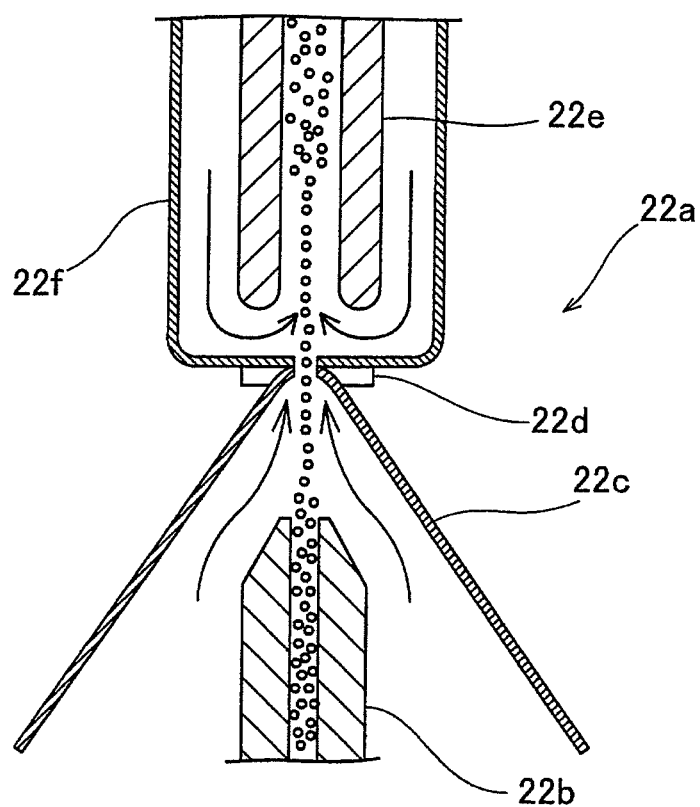
FIG. 11 is a schematic view showing the structure of the RBC detecting section.

The RBC detecting section 22 is a capable of counting the number of red blood cells and platelets using a sheath flow DC detection method. FIG. 11 is a schematic view showing the structure of the RBC detecting section. The RBC detection section 22 has a sheath flow cell 22a, as shown in FIG. 11. The sheath flow cell 22a is provided with a sample nozzle 22b which is open at the top so that a sample can be supplied from a sample supplying section to the sample nozzle 22b. The sheath flow cell 22a has a tapered chamber 22c which becomes narrower toward the top, and the sample nozzle 22b is disposed in the center of the interior of the chamber 22c. An aperture 22d is provided at the top end of the chamber 22c, and the aperture 22d coincides with the center position of the sample nozzle 22b. A sample supplied from the sample supplying section is fed upward from the tip of the sample nozzle 22b, and a front sheath liquid is simultaneously supplied to the chamber 22c so that the front sheath liquid flows upward toward the aperture 22d. The sample flows so as to be encapsulated in the front sheath liquid, and the sample flow is then constricted by the tapered chamber 22 so that the blood cells within the sample pass one by one through the aperture 22d. The aperture 22d is provided with electrodes and a direct current (DC) type of electric current is supplied between the electrodes. The change in the direct current resistance at the aperture 22d is detected when the sample flows through the aperture 22d, and the electrical signals are output to the analog processing section 52. The analog processing section 52 subjects the input electrical signals to amplification and waveform processing, and thereafter the processed electrical signals are output to the microcomputer 6. Since the direct current resistance increases when a blood cell flows through the aperture 22d, the electrical signal reflects information regarding the passage of the blood cell through the aperture 22d so that the number of red blood cells and platelets can be counted when the microcomputer 6 subjects the electrical signals to signal processing.

A collection tube 22e, which extends in a vertical direction, is provided above the aperture 22d. The collection tube 22e is disposed in the interior of a chamber 22f which is connected to the chamber 22c through the aperture 22d. The bottom end of the collection tube 22e is separated from the inner wall of the chamber 22e. The chamber 22f is configured to supply a back sheath liquid, and the back sheath liquid flows downward through the region on the outer side of the collection tube 22e of the chamber 22f. The back sheath liquid flowing on the outer side of the collection tube 22e reaches the bottom end of the chamber 22e, and thereafter flows between the inner wall of the chamber 22f and the bottom end of the collection tube 22e. The blood cells which have passed through the chamber 22d are thus prevented from creating a backflow, thereby avoiding erroneous detection of blood cells.

Figure 12:
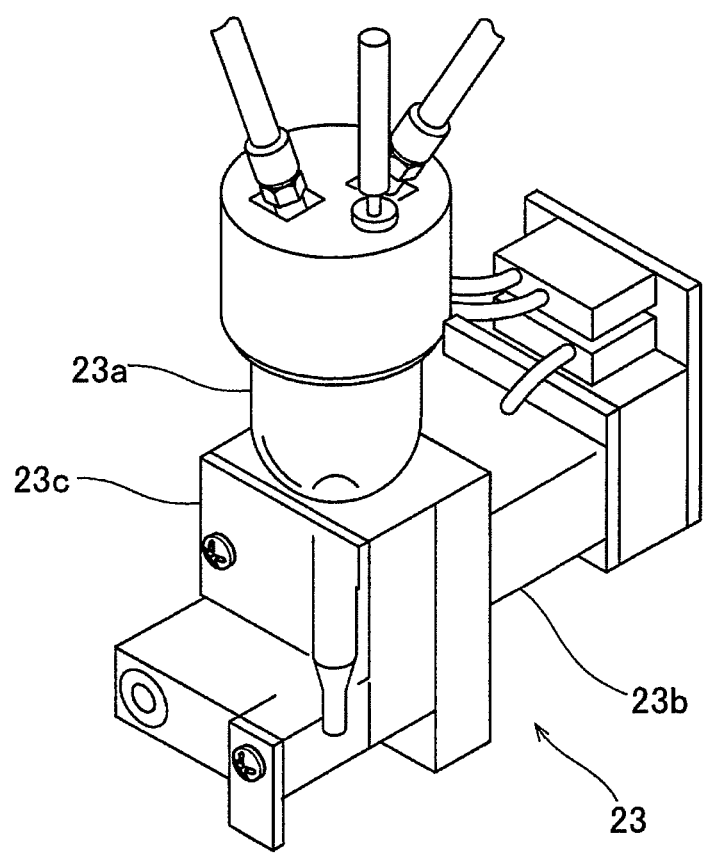
FIG. 12 is a schematic view showing the structure of the HGB detecting section.

The HGB detection section 23 is capable of measuring the amount of hemoglobin (HGB) using an SLS hemoglobin method. FIG. 12 is a perspective view which shows the structure of the HGB detection section 23. The HGB detection section 23 has a cell 23a for accommodating a dilute sample, a light-emitting diode 23b which emits light toward the cell 23a, and a photoreceptor element 23c which receives the light which passes through the cell 23a. An HGB measurement sample is prepared in the sampling valve 12 by diluting a fixed amount of blood to a predetermined dilution ratio using a dilution liquid (Cellpack (II), a product of Sysmex Corporation). The HGB measurement sample is supplied from the sampling valve 12 to the cell 23a, and accommodated therein. A predetermined hemolytic agent (sulfolyzer, a product of Sysmex Corporation) is introduced into the HGB detecting section 23, and the mixed with the HGB measurement sample within the cell 23a. The hemolytic agent has properties which transform the hemoglobin in the blood to SLS hemoglobin. In this state light is emitted from the light-emitting diode 23b and the transmission light is received by the photoreceptor element 23c which is disposed on the opposite side of the cell 23a facing the light-emitting diode 23b. The light-emitting diode 23b emits light which has a wavelength of high absorptivity by SLS hemoglobin, and since the cell 23a is configured of a plastic material which has a high degree of transmittancy, the transmittance light, which is only that light emitted from the light-emitting diode 23b that has been absorbed by the sample, is received by the photoreceptor element 23c. The photoreceptor element 23c outputs electrical signals corresponding to the amount of received light (absorbance) to the analog processing section 53, the electrical signals are then subjected to amplification processing and waveform processing, and the electrical signals which have been processed by the analog processing section 53 are then output to the microcomputer 6. The microcomputer 6 compares this absorbance with the absorbance of the dilution liquid alone which was previously measured.

Figure 13:
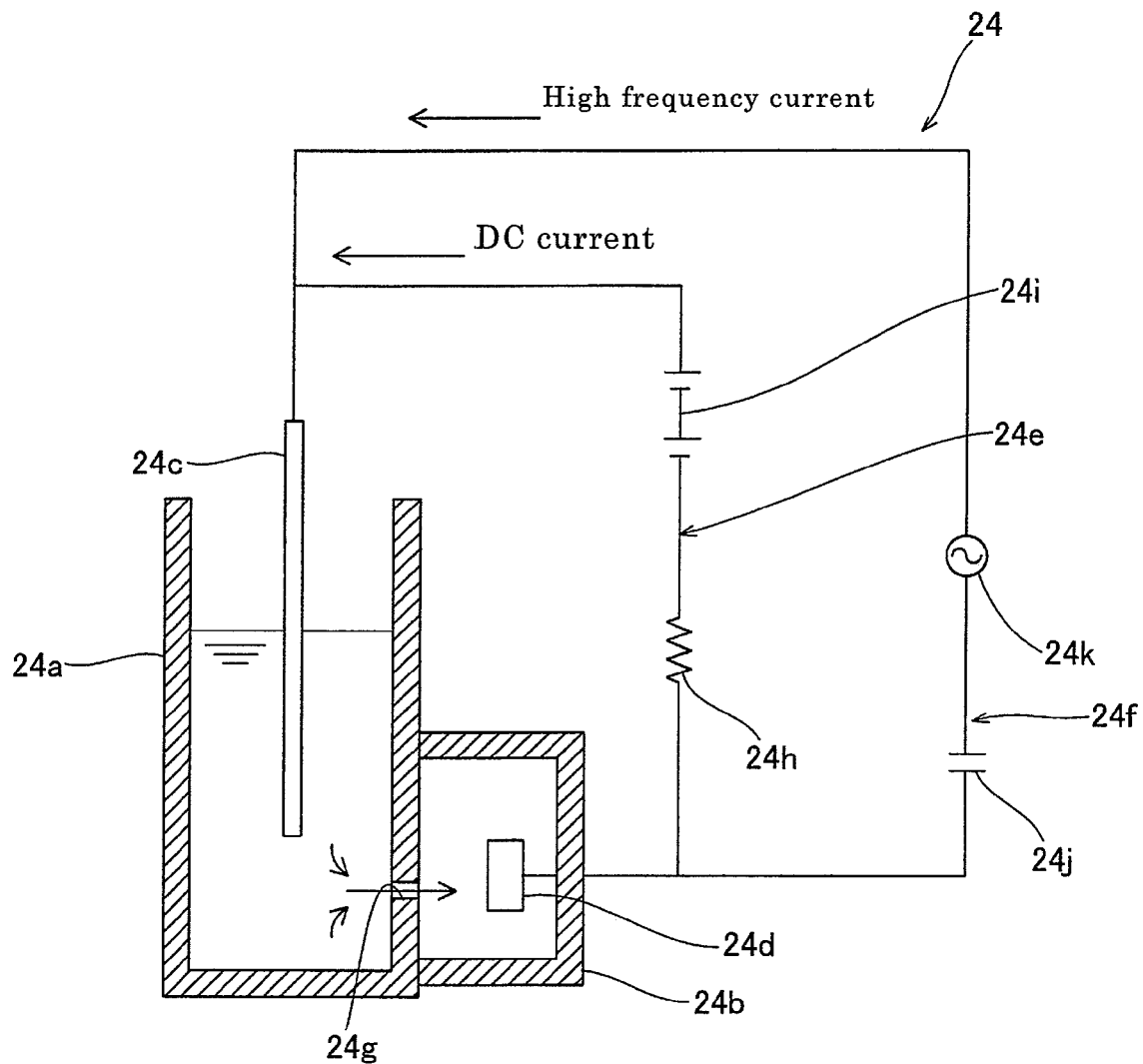
FIG. 13 is a schematic view showing the structure of the IMI detecting section.

The IMI detecting section 24 is capable of measuring the incidence of immature cells in the sample using an RF/DC detection method. FIG. 13 is a schematic view showing the structure of the IMI detecting section 24. The IMI detecting section 24 has a detecting chamber 24a, an aspirating chamber 24b, a direct current (DC) supplying circuit 24e which is connected to the electrodes 24c and 24d, and a high-frequency current supplying circuit 24f which is connected to the electrodes 24c and 24d. A fixed amount of sample, which has been aspirated by the sample supplying section and diluted a predetermined amount is supplied to the detecting chamber 24a. The detecting chamber 24a is adjacent to the aspirating chamber 24b, and both chambers 24a and 24b are connected via an aperture 24g. The aspirating section 24b is connected to a pump which is not shown in the drawing, so that dilute sample c an be aspirated by this pump. The aspirated dilute sample flows from the detecting chamber 24a into the aspirating chamber 24b through the aperture 24g. The electrode 24c is provided within the detecting chamber 24a, and the electrode 24d is provided within the aspirating chamber 24b. The DC electric current supplying circuit 24e is connected in series with a resistor 24h and a DC power source 24i so as to supply a DC electric current between the electrodes 24c and 24d. Thus, when the dilute sample is aspirated by the pump, blood cells contained in the dilute sample pass through the aperture 24g, whereupon there is a change in the DC resistance between the electrodes 24c and 24d. The electrical signals which have been changed by the DC resistance are then output from the DC electrical current supplying circuit 24e to the analog processing section 54. The change in the DC resistance reflects information relating to the size of the blood cell which passed through the aperture 24g, and the microcomputer 6 obtains the size of the blood cell by subjecting this electrical signal to signal processing.

The high-frequency DC electrical current supplying circuit 24f is connected in series with a capacitor 24j and a high frequency power source 24k so as to supply a high frequency electrical current between the electrodes 24c and 24d. Thus, when the dilute sample is aspirated by the pump, blood cells contained in the dilute sample pass through the aperture 24g, whereupon there is a change in the high frequency resistance between the electrodes 24c and 24d. The electrical signals representing the change in the high frequency resistance are output from the high-frequency electrical current supplying circuit 24f to the analog processing section 54. The analog processing section 54 subjects the electrical signals to amplification processing and waveform processing, and outputs the processed electrical signals to the microcomputer 6. The change in the high-frequency resistance reflects information regarding the density of the interior of the blood cell that has passed through the aperture 24g, and the microcomputer 6 obtains the interior density of the blood cell by subjecting the electrical signals to signal processing.

As shown in FIG. 2, the microcomputer 6 mainly includes an A/D converter 6a, an arithmetic logic unit 6b, an external connection interface 6c, and a controller 6d. The A/D converter 6a has the function of converting the analog waveform signal received from the analog processing section 54 to a digital waveform signal. The arithmetic logic unit 6b is connected to the A/D converter 6a, and has the function of executing predetermined computer programs to process the digital waveform signals. The controller 6d is configured by a control processor, and a memory for operating the control processor. The controller 6d has the function of controlling the device 8, which is configured by a fluid system to adjust and measure samples, and a sampler (not shown in the drawing) to automatically supply the collection tubes 11 (refer to FIG. 3), and perform other controls.

The microcomputer 6 includes a distribution map generator 6e configured by a processor to create distribution maps and a memory for the operation of the processor that creates distribution maps. The distribution map generator 6e has the function of creating two-dimensional scattergrams based on the output of the optical detecting section 4. The distribution map generator 6e is connected to the data processing section 3 through the external connection interface 6c, and is configured to sent measurement results, such as a generated scattergram and the like, to the data processing section 3.

The microcomputer 6 is provided with a bus 6f and a plurality of other interfaces, so that the digital waveform signals calculated in the arithmetic logic unit 6b are transmitted to the data processing section 3 through the interface 6g, the bus 6f, the controller 6d, the bus 6h, the distribution map generator 6e, and the external connection interface 6c. The display and operation section 7, and the device 8 for performing blood measurements are also connected to the bus 6f through an interface 6i and an interface 6j, respectively.

The measuring section 2 which has the previously described structure performs measurements of the four white blood cell classifications to classify lymphocytes (LYMPH), monocytes (MONO), neutrophils (NEUT), and eosinophil+ basophil groups (EO+BASO). Other white blood cells are classified as basophils (BASO) via the previously mentioned WBC/BASO measurement. Based on these results the white blood cells can be classified into five groups which include lymphocytes (LYMPH), monocytes (MONO), neutrophils (NEUT), basophils (BASO), and eosinophils (EO), the number of white blood cells in each groups can be counted, and percentage of white blood cells included in each group can be calculated relative to the total number of white blood cells. The number of red blood cells (RBC) and the number of platelets (PLT) are respectively counted by the previously mentioned RBC/PLT measurement, and the hematocrit value (HCT) is also measured. The hemoglobin value (HGB) is also measured by the previously mentioned HGB measurement. The microcomputer 6 calculates the mean corpuscular volume (MCV) from the HCT and RBC, calculates the mean corpuscular hemoglobin (MCH) from the HGB and RBC, and calculates the mean corpuscular hemoglobin concentration (MCHC) from the HGB and HCT. The immature erythrocytes (IMI) are counted by differentiating the mature cells and the immature white blood cells using the previously mentioned IMI measurement. The nucleated red blood cells (NRBC) are counted by differentiating the white blood cells and the nucleated red blood cells using the previously mentioned NRBC measurement. The number of reticulocytes (RET#), number of mature red blood cells, and the number of platelets are counted by differentiating the mature red blood cells, the reticulocytes, and the platelets using the previously mentioned RET measurement. The microcomputer 6 calculates the percentage of reticulocytes (RET %) from the number of mature red blood cells and the number of reticulocytes; then calculates the highly fluorescent reticulocyte percentage (HFR) which is the percentage of reticulocytes that appear in the region of high fluorescent intensity, the intermediate fluorescence reticulocyte percentage (MFR) which is the percentage of reticulocytes that appear in the region of intermediate fluorescent intensity, and the low fluorescence reticulocyte percentage (LFR) which is the percentage of reticulocytes that appear in the region of low fluorescent intensity; and finally calculates the immature platelet percentage (IPF) which is the percentage of immature platelets relative to the total number of platelets appearing a predetermined region in the scattergram of the RET measurement result obtained when the side fluorescent light intensity is plotted on the X axis and the side scattered light intensity is plotted on the Y axis. The microcomputer 6 also calculates the hemoglobin concentration index within the reticulocyte (RET-He) using the RET measurement result, and then calculates the percentage in the hematopoietic progenitor cell monitoring region (HPC %). The microcomputer 6 also calculates the number of cells in the hematopoietic progenitor cell monitoring region (HPC#) from the HPC % and the WBC, calculates the fragmentocyte percentage (FRC %) from the RET measurement result and calculates the number of fragmentocytes (FRC#) from the FRC % and the RBC. The immature granulocyte percentage (IG %) is also calculated from the 4DIFF measurement result, and the number of immature granulocytes (IG#) is calculated from the IG % and the WBC. The microcomputer 6 determines the RBC granularity distribution, then calculates the 20% frequency level distribution width RDW-SD when the peak height is set at 100% from the granularity distribution, and calculates the center distribution width RDW-CV of a predetermined frequency of the total granularity area in the granularity distribution. The microcomputer 6 also determines the PLT granularity distribution, then calculates the 20% frequency level distribution width PDW when the peak height is set at 100% from the granularity distribution, and calculates the percentage of large platelets P-LCR or determines the platelet crit value (PCT) by weighting the PLT frequency, and calculating the mean platelet volume (MPV) from the PCT and PLT.

The measuring section 2 is capable of measuring items such as CBC, granularity distribution analysis items, DIFF, RET, and NRBC. The CBC is a group of measurement items which includes white blood cell count (WBC), red blood cell count (RBC), hemoglobin (HGB), hematocrit (HCT), mean corpuscular volume (MCV), mean corpuscular hemoglobin (MCH), mean corpuscular hemoglobin concentration (MCHC), and platelet count (PLT); and the granularity distribution analysis is a group of measurement items which includes red blood cell distribution width (RDW-SD), red blood cell distribution width (RDW-CV), platelet distribution width (PDW), mean platelet volume (MPV), large platelet percentage (P-LCR), and platelet crit value (PCT). The DIFF is a group of measurement items which includes the neutrophil percentage (NEUT %), lymphocyte percentage (LYMPH %), monocyte percentage (MONO %), eosinophil percentage (EO %), basophil percentage (BASO %), neutrophil count (NEUT#), lymphocyte count (LYMPH#), monocyte count (MONO#), eosinophil count (EO#), basophil count (BASO#). The RET is a group of measurement items which includes the reticulocyte percentage (RET %), reticulocyte count (RET#), high fluorescence reticulocyte percentage (HFR), intermediate fluorescence reticulocyte percentage (MFR), low fluorescence reticulocyte percentage (LFR), and reticulocyte maturity index (IRF). The NRBC is a group of measurement items which includes the nucleated red blood cell percentage (NRBC %) and nucleated red blood cell count (NRBC#). The measuring section 2 is configured to be capable of measuring items such as immature platelet percentage (IPF), hemoglobin concentration index within reticulocytes (RET-He), immature granulocyte percentage (IG %), immature granulocyte count (IC#), percentage in the hematopoietic progenitor cell monitoring region (HPC %), number in the hematopoietic cell monitoring region (HPC#), fragmentocyte percentage (FRC %), and fragmentocyte count (FRC#).

The data processing section 3 (refer to FIG. 1) is configured by a personal computer (PC) which includes a controller 301 that incorporates a CPU, ROM, and RAM, a display unit 302, and an input device 303, as shown in FIG. 1. The display unit 302 is provided to display the analysis results obtained by analyzing the digital signal data received from the microcomputer 6 (refer to FIG. 2) of the measuring section 2. In the present embodiment, the data processing section 3 is capable of providing the user with information which assists in the diagnosis when a user such as a physician or the like is making a diagnosis based on the obtained analysis results. That is, the data processing section 3 is configured to judge the possibility that a patient has a blood disease based on the analysis results, and to display information related to the disease when the data processing section 3 has judged there is a possibility that the patient has a blood disease. The display of the information related to such disease is described in detail later.

Figure 14:
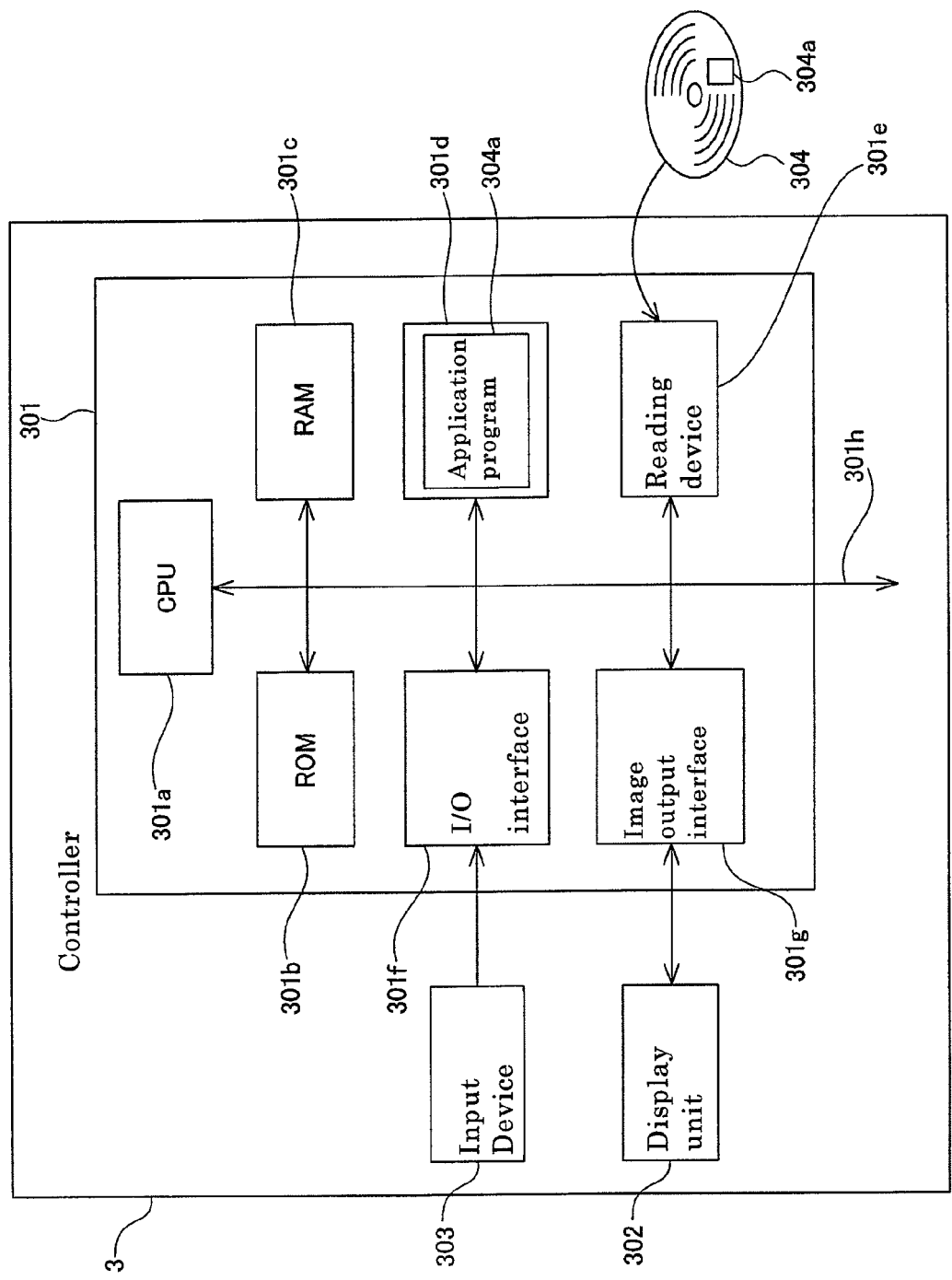
FIG. 14 is a block diagram showing the data processing section of the blood analyzer of FIG. 1.

The structure of the data processing section 3 is described below. As shown in FIG. 14, the data processing section 3 is a computer mainly configured by a controller 301, a display unit 302, and an input device 303. The controller 301 is mainly configured by a CPU 301a, ROM 301b, RAM 301c, hard disk 301d, reading device 301e, input/output device 301f, and image output interface 301g. The CPU 301a, ROM 301b, RAM 301c, hard disk 301d, reading device 301e, input/output interface 301f, and image output interface 301g are connected by a bus 301h.

The CPU 301a is capable of executing computer programs stored in the ROM 301b, and computer programs loaded in the RAM 301c. The computer functions as the data processing section 3 when the CPU 301a executes an application program 304a which is described later.

The ROM 301b is configured by a mask ROM, PROM, EPROM, EEPROM or the like, and stores computer programs executed by the CPU 301a and data and the like used in conjunction therewith.

The RAM 301c is configured by SRAM, DRAM or the like. The RAM 301c is used when reading the computer program recorded in the ROM 301b and on the hard drive 301d. The RAM 301c is also used as a work area of the CPU 301a when the computer program is being executed.

The hard drive 301d contains various installed computer programs to be executed by the CPU 301a such as an operating system and application program and the like, as well as data used in the execution of these computer programs. Also installed on the hard disk 301d is the application program 304a which will be described later.

The reading device 301e is configured by a floppy disk drive, CD-ROM drive, DVD-ROM drive or the like, and is capable of reading the computer programs and data stored on a portable recording medium 304. The portable recording medium 304 stores the application program 304a which realizes the predetermined functions on a computer, and the application 304a is read from the portable recording medium 304 by the computer functioning as the data processing section 3, and the application program 304a is installed on the hard disk 301d.

The application program 304a is not only provided the portable recording medium 304 inasmuch as the application program 304a may also be provided from an external device which is connected to the data processing section 3 over an electric communication line so as to be capable of communication via this electric communication line (whether wire line or wireless). For example, when the application program 304a is stored on the hard disk of a server computer on the Internet, the data processing section 3 accesses the server computer and downloads the application program 304a, which is then installed on the hard disk 301d.

An operating system which provides a graphical user interface, such as Windows (registered trademark) or the like, a product of Microsoft Corporation, USA, is installed on the hard disk 301d. The application program 304a of the present embodiment operates on this operating system in the following description.

The input/output interface 301f is configured, for example, by a serial interface such as a USB, IEEE1394, RS232C or the like, a parallel interface such as SCSI, IDE, IEEE1284 or the like, and an analog interface such as a D/A converter, A/D converter or the like. The input device 303, which includes a keyboard and mouse, is connected to the input/output interface 301f, so that a user can input data in the data processing section 3 using the input device 303.

The image output interface 301g is connected to the display unit 302 which is configured by an LCD, CRT or the like, so that image signals corresponding to the image data received from the CPU 301a can be output to the display unit 302. The display unit 302 displays images (screens) in accordance with the input image signals.

Figure 15:
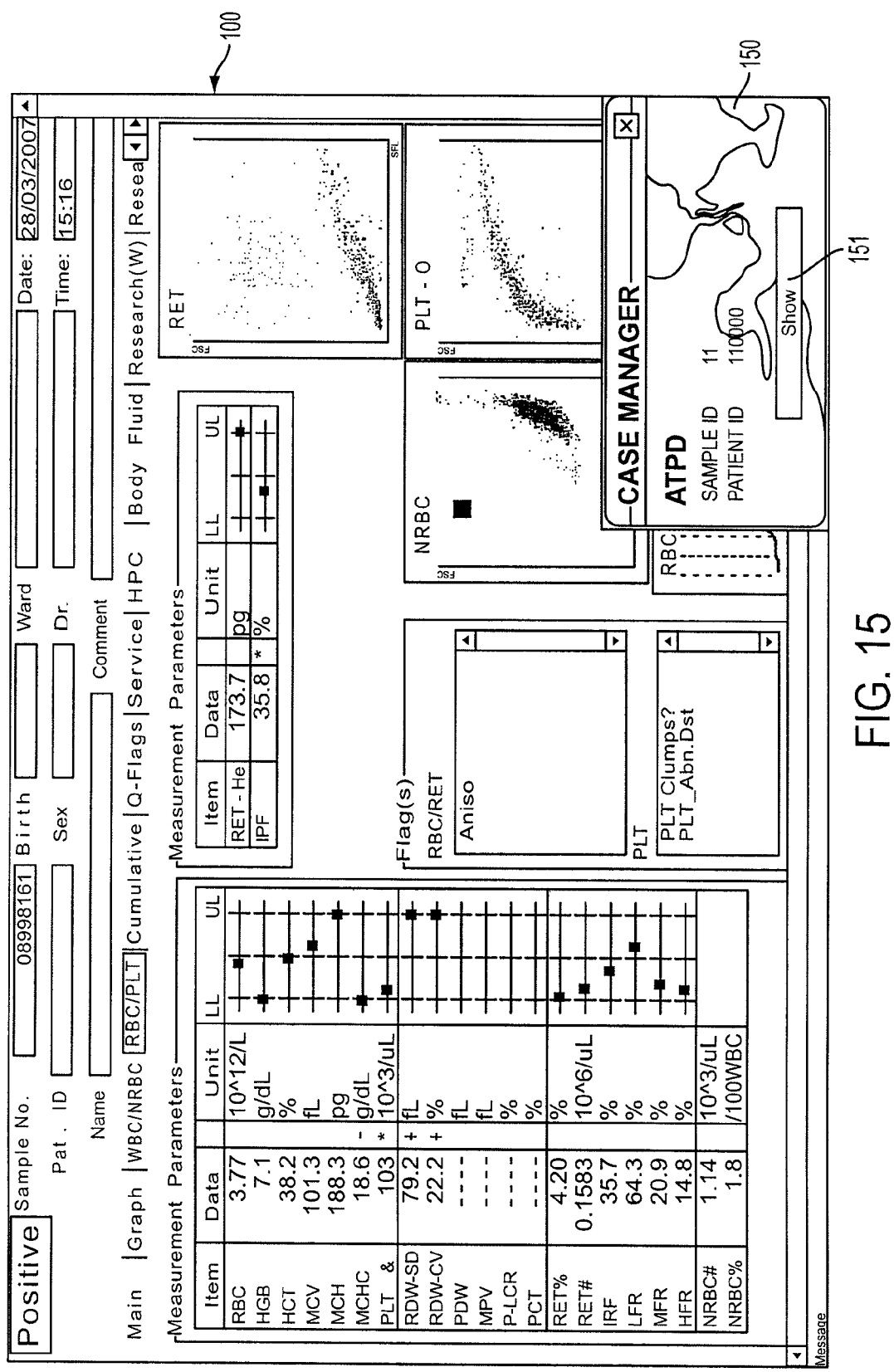
FIG. 15 shows an analysis result display screen and a notification display screen which are displayed on the display unit of the data processing section.
Figure 16:
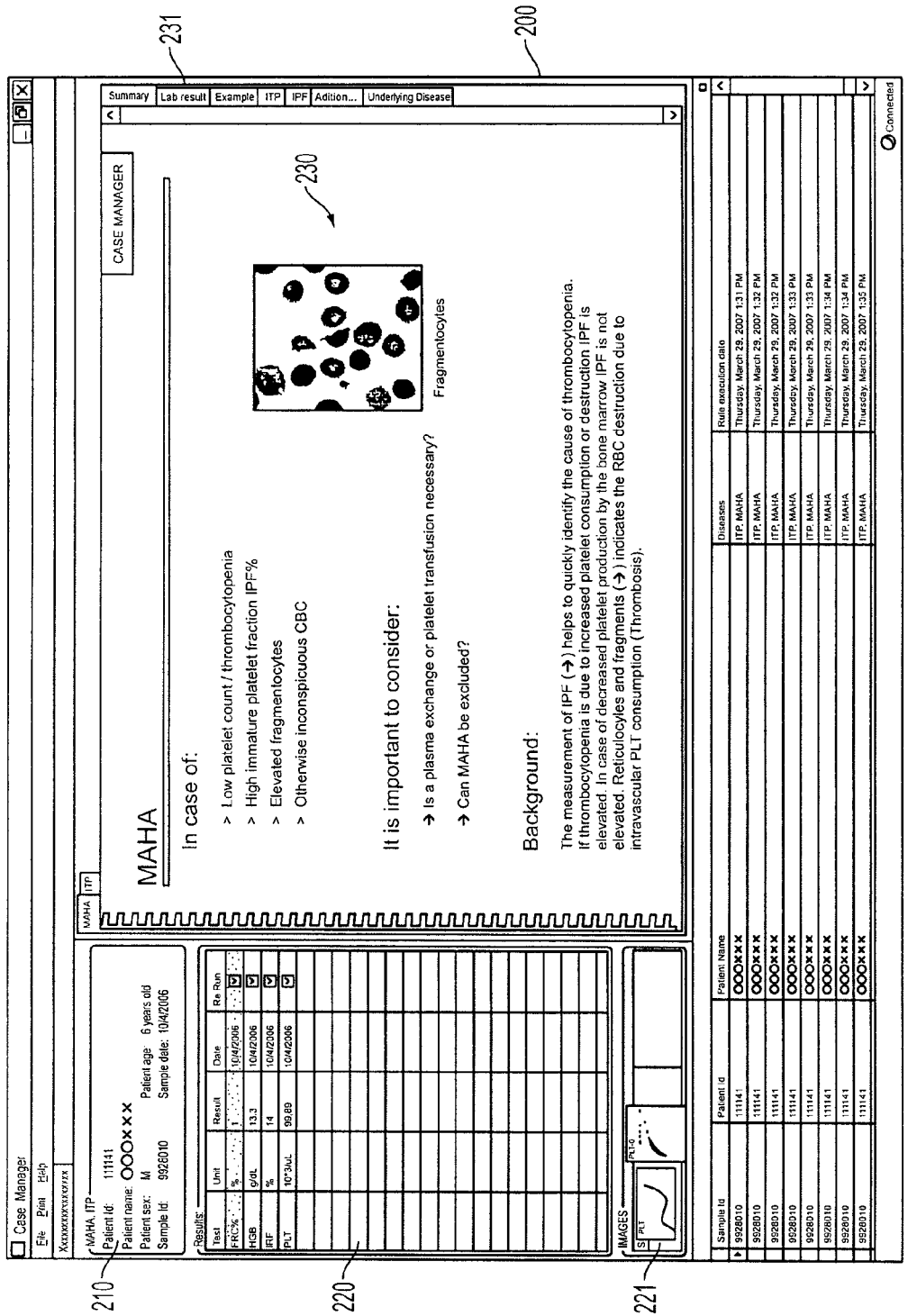
FIG. 16 shows a diagnosis assisting information screen which is displayed on the display unit of the data processing section.
Figure 17:
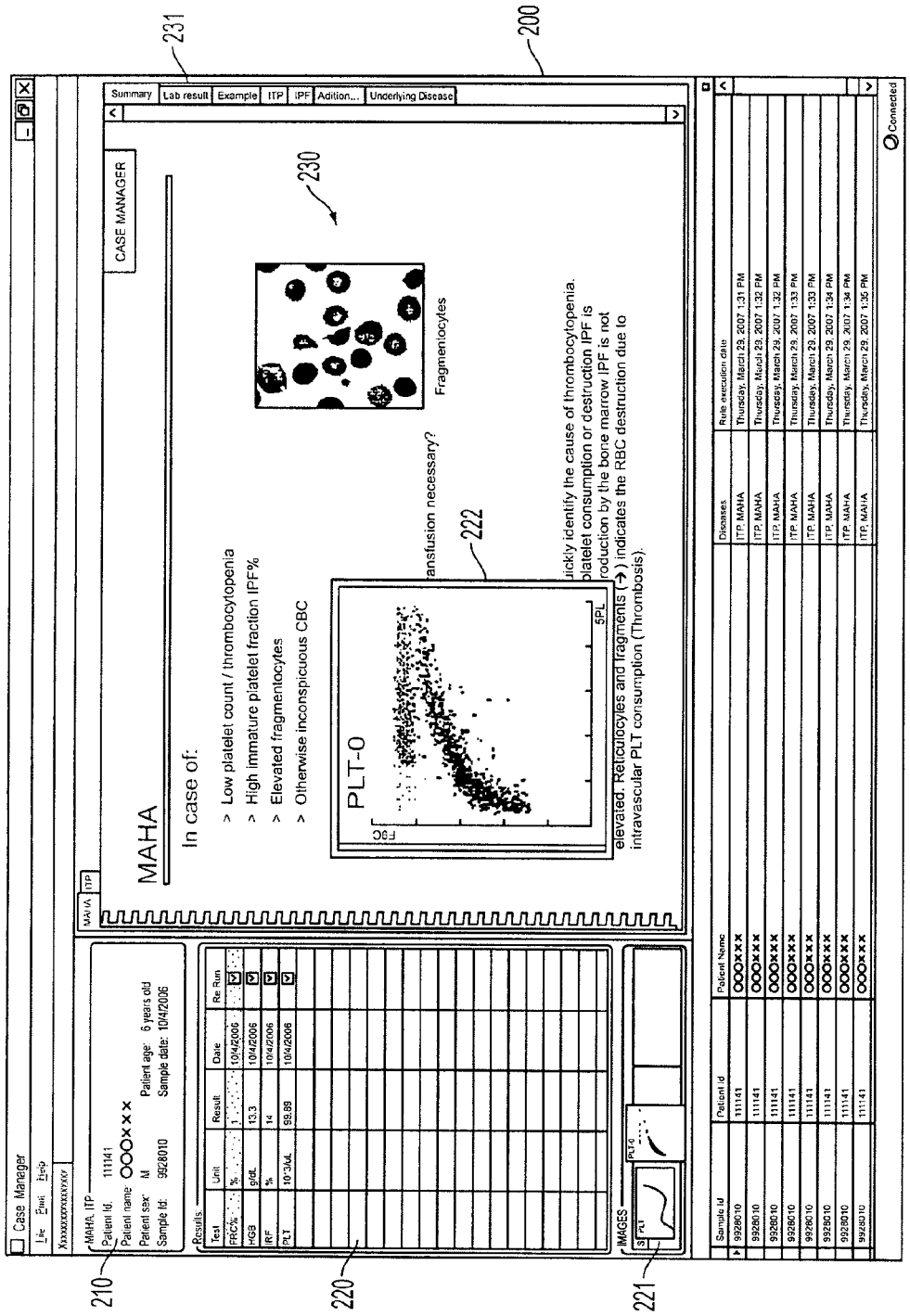
FIG. 17 shows a diagnosis assisting information screen when and enlarged analysis result graph is displayed.

FIG. 15 shows an analysis result display screen of the blood analyzer using the diagnosis assisting system of the present embodiment. FIGS. 16 and 17 show diagnosis assisting information display screen of the diagnosis assisting system. FIGS. 18 through 27 are screens which show various information displayed in the diagnosis assisting information display regions of the diagnosis assisting information display screen. The content of the diagnosis assisting information and the structure of the screens of the diagnosis assisting system of the present embodiment are described below with reference to FIGS. 15 through 27. Examples of judging when a patient has a disease called "MAHA (Microangiopathic haemolytic anaemia)", and a disease called "HELLP-Syndrom (Haemolysis with elevated liver enzyme concentration in serum of low platelet counts)" are described below.

As shown in FIG. 15, the analysis result display screen 100 is displayed when the analysis is completed. The measurement results (numerical values) such as CBC, DIFF, RET, NRBC, and IPF are displayed on the analysis result display screen 100. Also displayed are graphs such as a histogram created by the data processing section 3, and scattergram created by the distribution map generator 6e.

In the present embodiment, the application program 304a determines whether or not the obtained analysis result satisfies the conditions of each disease included beforehand in the application program 304a. When it has been determined that conditions of a disease are satisfied, a notification screen 150 is displayed, as shown in FIG. 15. The conditions concerning "MAHA" include that the PLT, WBC, HGB, IPF, RET, IRF, and FRC values are outside predetermined ranges in addition to the measurement items including CBC, DIFF, and RET, and that there is no platelet aggregation in the sample. Conditions concerning "HELLP-Syndrom" include that the patient is hospitalized for childbirth, the values of PLT, WBC, HGB, IPF, RET, IRF, and MCH are outside predetermined ranges in addition to the measurement items including CBC, DIFF, and RET, and that there is no platelet aggregation in the sample. Other diseases have respectively different conditions.

As shown in FIG. 15, a call button 151 ("show" in FIG. 15) is provided in the notification screen 150. When the call button 151 is selected by the user, the diagnosis assisting information screen 200 is displayed, as shown in FIG. 16.

The diagnosis assisting information screen 200 includes a sample attribute information display region 210, an analysis result display region 220, and a disease information display region 230.

Information which identifies the patient and the sample collected from the patient is displayed in the sample attribute information display region 210. Specifically, the patient management number, name, sex, and age, as well as the sample management number, and date of sample collection are displayed in the sample attribute information display region 210.

Some of the numerical values of the analysis results, and thumbnails 221 of the analysis result scattergram and histogram graphs are displayed in the analysis result display region 220, as shown in FIG. 15.

The scattergram and the graphs can be enlarged and displayed by double clicking the thumbnail 221, as shown in FIG. 17. The enlarged scattergram and graphs 222 can be dragged by the mouse (not shown in the drawing). The user can thus visually compare the enlarged graphs 222 with the content of the disease information display region 230.

Information related to the disease which the patient is judged possibly have is displayed in the disease information display region 230 by the application program 304a. The configuration when "MAHA" is displayed in the disease information display region 230 is described below.

"MAHA": The disease information display region 230 is provided with various tabs 231 which include "summary," "example," "lab result," "TTP," "IPF," "additional information," and "underlying disease." Information corresponding to the tab 231 can be displayed in the disease information display region 230 by selecting the tab 231. As shown in FIG. 16, the initial display of the diagnosis assisting information screen 200 is displayed with the tab "summary" selected. The diagnosis assisting information corresponding to each tab is described below.

As shown in FIG. 18, a summary of the disease "MAHA" is described in the "summary." That is, the characteristics or trends of "MAHA" are described in the "In case of . . . " section. For example, characteristics include low platelet count and thrombocytopenia. Messages pertaining to considerations concerning the possibility of other diseases and methods of treating "MAHA" are provided in the "It is important to consider" section. A suggestion of the efficacy of IPF in identifying the cause thrombocytopenia is provided in the "Background" section.

As shown in FIG. 19, the "example" section provides specific cases of fictitious patients, examination results, diagnostic process and the like.

As shown in FIG. 20, the "lab result" section provides a stained blood sample image and typical graphs (scattergram and histogram) representing the characteristics of "MAHA." A graph of a healthy subject is provided for comparison. In FIG. 20, for example, a histogram representing an abnormal platelet count, a scattergram representing IPF, a scattergram representing the red cell count, and a stained sample image of immature platelets and fragmentocytes. The user can simultaneously visually compare these graphs and the enlarged graphs 222 of the analysis results (FIG. 17).

As shown in FIG. 21, the "underlying disease" section provides an description of other diseases medically classified in the same group. "MAHA" is one type of hemolytic anemia caused by a vascular constriction. As shown in FIG. 22, a description of "TTP" which is a disease related to "MAHA" is described in the "TTP" section. As shown in FIG. 23, a description of "IPF" is provided in the "IPF" section.

As shown in FIG. 24, information related to reference materials such as literature concerning "MAHA" is provided in the "additional information" section. Specifically, information concerning literature related to fragmentocytes, literature related to platelets, and literature related to IPF are shown in FIG. 24.

"HELLP-Syndrom": The configuration of the disease information display region of "HELLP-Syndrom" is described below.

In the case of "HELLP-Syndrom," the disease information display region (not shown in the drawing) is provided with various tabs (not shown in the drawing) including "summary," "example," "lab results," "additional information," and "underlying disease."

As shown in FIG. 25, a summary of the disease "HELLP-Syndrom" is displayed in the "summary" section. That is, the characteristics or trends of "HELLP-Syndrom" are displayed in the "In case of . . . " section. For example, characteristics include thrombocytopenia in pregnant women and high IPF %. Since "HELLP-Syndrom" can threaten the life of both the mother and fetus, the need for quick diagnosis and treatment is provided in the "It is important to consider" section. A suggestion of the efficacy of IPF in identifying the cause thrombocytopenia is provided in the "Background" section.

As shown in FIG. 26, the "example" section provides documents such as specific cases of fictitious patients, examination results, diagnostic process and the like for "HELLP-Syndrom." As shown in FIG. 27, the "lab result" section displays graphs (scattergram and histogram), and blood sample smear image showing the characteristics of "HELLP-Syndrom." The "underlying disease" and "additional information" sections contain the same content as the "underlying disease" and "additional information" sections for "MAHA" shown in FIGS. 21 and 24.

Figure 28:
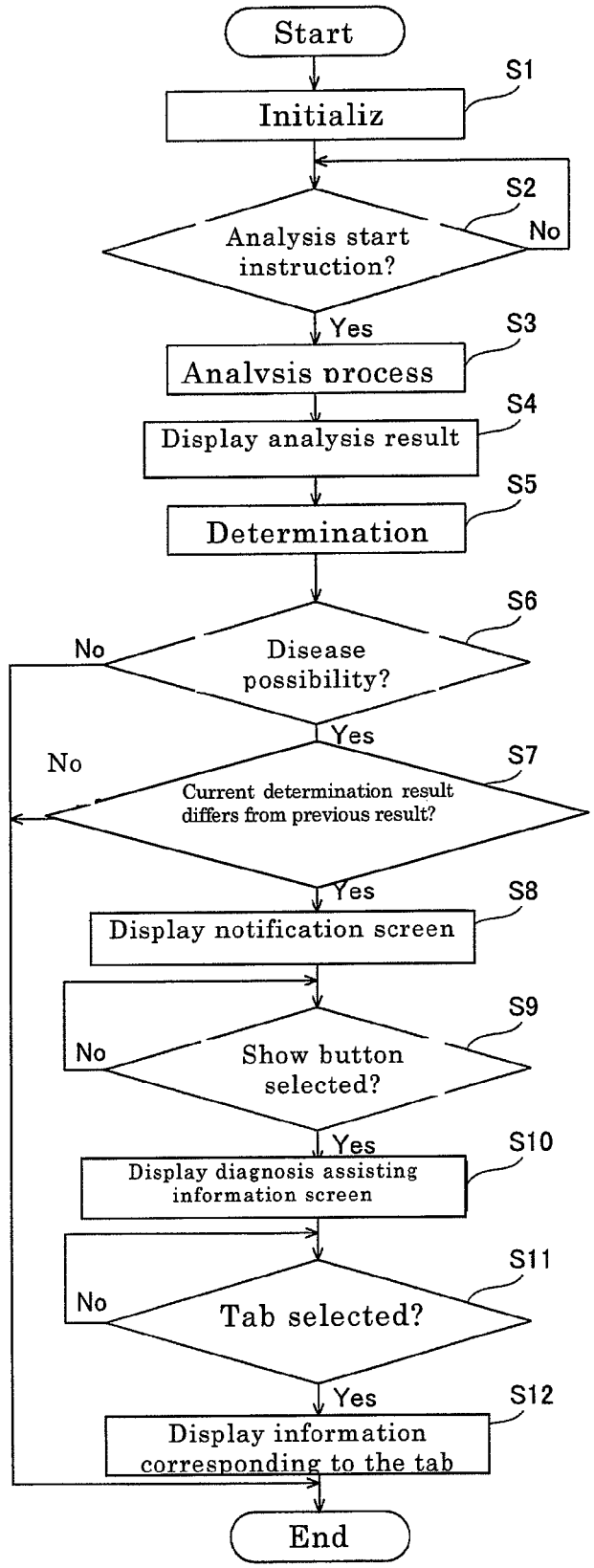
FIG. 28 is a flow chart illustrating the diagnosis assisting operation display operation of the blood analyzer of FIG. 1.

FIG. 28 is a flow chart illustrating the operation of displaying the diagnosis assisting information of the blood analyzer using the diagnosis assisting system of the present embodiment. The diagnosis assisting information display operation of the blood analyzer 1 is described below with reference to FIGS. 1, 5, 16, and 28.

When the main switch (not shown) of the measuring section 2 (refer to FIG. 1) is turned ON in step S1 of FIG. 28, the controller 6d of the measuring section 2 is initialized and an operation check is performed for each part of the measuring section 2.

Thereafter, the user issues an instruction to start analysis in the data processing section 3. In step S2, a determination is made as to whether or not an analysis start instruction has been received. That is, the controller 6d of the measuring section 2 determines whether or not the measuring section 2 has received an analysis start instruction sent from the data processing section 3 by the user operating the data processing section 3. When an analysis start instruction has not been received, the determination is repeated. When an analysis start instruction has been received, the analysis process is performed in step S3. In the analysis process, IPF, RET-He, HPC, IG, and FRC are measured in addition to CBC, DIFF, RET, and NRBC.

Thereafter, the analysis result display screen 100 is displayed in step S4, as shown in FIG. 15. The controller 301 of the data processing section 3 determines whether there is a possibility that the subject has a disease by determining whether or not the previously described conditions are satisfied based on the obtained analysis results in step S5.

When the determination is that there is no possibility of disease, the diagnosis assisting information is not displayed and the process ends in step S6. When a possibility of disease has been determined, the controller 302 of the data processing section 3 determines whether or not there is a difference between the current determination result and the previous determination result in step S7. That is, when the current determination is not the first determination, a determination is made as to whether or not the current determination result differs from the previous determination result. Since there is no need to display diagnosis assisting information when the current determination result and the previous determination result are the same, the process ends without displaying the diagnosis assisting information. When the current determination result differs from the previous determination result, the notification screen 150 is displayed in step S8, as shown in FIG. 15. The user can verify the possibility of a subject having a disease by displaying the notification screen 150. The user selects the call button 151 of the notification screen 150 when the user wants to consider the diagnosis assisting information.

The controller 301 of the data processing section 3 determines whether or not the call button 151 has been selected in step S9. When the call button 151 has not been selected, the determination is repeated. When the call button has been selected, the diagnosis assisting information screen 200 is displayed in step S10 as shown in FIG. 16. The diagnosis assisting information screen 200 initially displays the "summary" tab. The user may thereafter switch the display to the diagnosis assisting information region 230 by selecting the tab 231.

The controller 301 of the data processing section 3 determines whether or not the tab 231 has been selected in step S11. When the tab 231 has not been selected, the determination is repeated. When the tab 231 has been selected, the information corresponding to the selected tab 231 is displayed on the diagnosis assisting information display region 230 in step S12.

Thus, the diagnosis assisting information is displayed by the diagnosis assisting system of the present embodiment.

When it has been determined that there is a possibility that the subject has a specific disease in the present embodiment, a user such as a physician can confirm the possibility that the subject has a disease by displaying the notification screen 150 because the notification screen 150 which includes the call button 151 is displayed on the display unit 302. When the user wants to consult the diagnosis assisting information, the user can operate the call button 151 to display the diagnosis assisting information screen 200 related to the disease which the subject might have on the display unit 302. Since the user can refer to the diagnosis assisting information screen 200 when making a diagnosis, the user can obtain knowledge of the disease from the diagnosis assisting information screen 200 when the user lacks sufficient knowledge of the disease. A user such as a physician can therefore rapidly and accurately diagnose a disease from the analysis results.

In the present embodiment, the user can confirm the possibility of a subject having a disease, and the characteristics of the disease ( ) by looking at the disease information display region 230 when the name of the disease such as "MAHA" and the characteristics of the disease are displayed in the disease information display region 230.

In the present embodiment, the user desires to know details of a disease, the information can be obtained from reference materials such as essays and research material on the disease by displaying the information related to the disease in the disease information display region 230.

A user can refer to typical graphs and images which represent the characteristics of a disease when making a diagnosis by displaying images (sample smear image) and typical graphs (scattergram and histogram) representing the characteristics of a disease in the disease information display region.

In the present embodiment, when making a diagnosis a user can compare information related to a disease with graphs of the analysis results in the diagnosis assisting information screen 200, since the user can confirm graphs (scattergram and histogram) of the analysis results in the diagnosis assisting information screen 200.

The embodiment of the present disclosure is an example in all aspects and is not to be considered as limiting in any way. The scope of the present invention is defined by the scope of the claims and not be the description of the embodiment, and includes all modifications within the scope of the claims and the meanings and equivalences therein.

Figure 29:
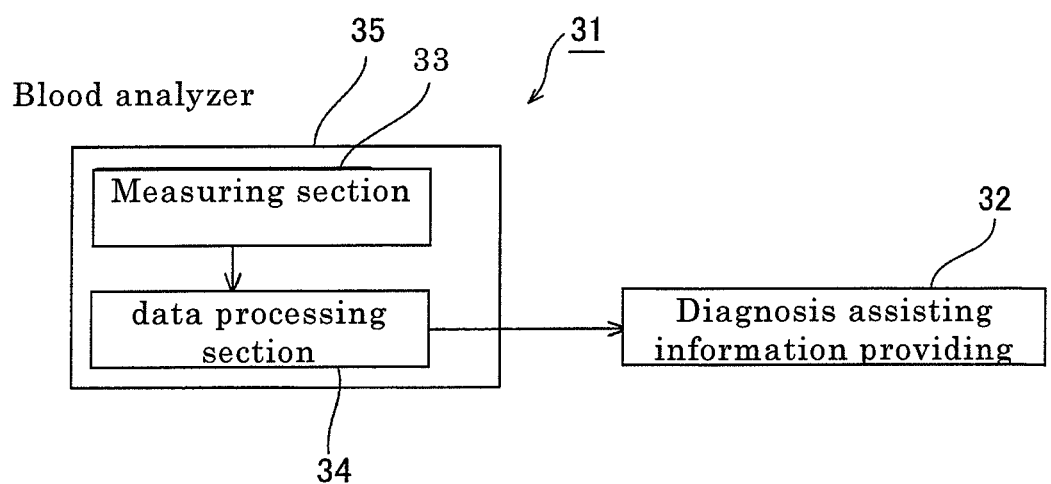
FIG. 29 is a block diagram of a first modification of the diagnosis assisting system of the present embodiment.

For example, although the above embodiment describes an example in which a function to display diagnosis assisting information is provided in the data processing section 3 of a blood analyzer 1 which is configured by the data processing section 3 and a measuring section 2, the present invention is not limited to this arrangement inasmuch as a dedicated device ( ) may also be provided to display the diagnosis assisting information as in the diagnosis assisting system of a first modification shown in FIG. 29. A diagnosis assisting information device 32 is configured by a personal computer, and is connected to a blood analyzer 35 which is configured by a measuring section 33 and a data processing section 34. The diagnosis assisting information device 32 has an obtaining means to obtain sample analysis results from the data processing section 34. The diagnosis assisting information device 32 includes programs to determine whether there is a possibility that a subject has a disease based on the obtained analysis results, and display the diagnosis assisting information. The diagnosis assisting information device 32 therefore has functions similar to the functions of displaying diagnosis assisting information of the data processing section 34 of the embodiment.

Although the embodiment provides an example of displaying a notification screen 150 only when the current determination result differs from the previous determination result, the present invention is not limited to this arrangement inasmuch as the notification screen 150 may also be displayed when the determination results are identical. Furthermore, a configuration may be employed in which an optional diagnosis assisting information screen 200 can be called up and displayed when the user performs a predetermined operation.

Although the above embodiment provides an example of the present invention applied to a blood analyzer 1 which analyzes the types the number of blood cells, the present invention is not limited to this arrangement inasmuch as the present invention is also applicable to other analyzers such as blood coagulation measuring devices, immunoanalyzers, biochemical analyzers and the like.

Figure 30:
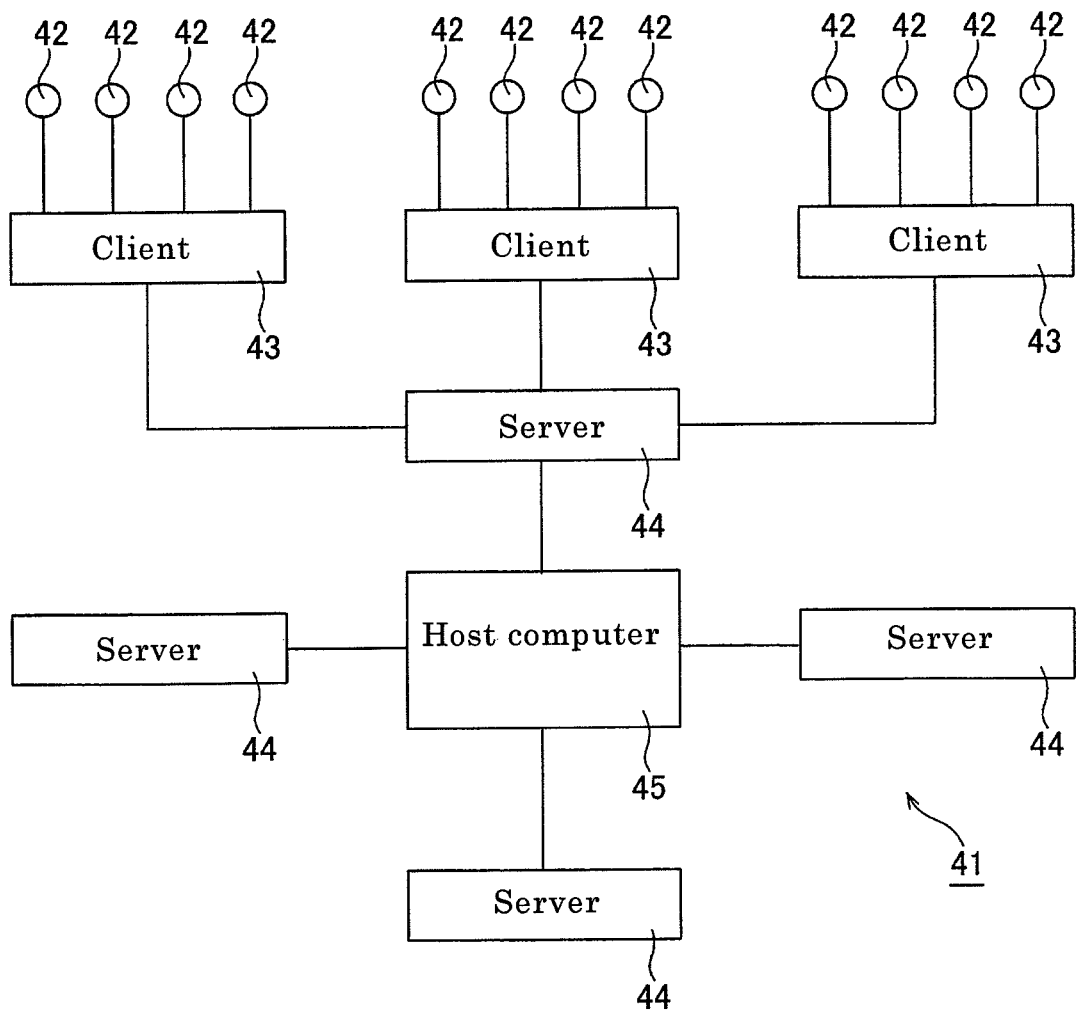
FIG. 30 is a block diagram of a second modification of the diagnosis assisting system of the present embodiment.

Although the above embodiment provides an example of the diagnosis assisting system applied to a blood analyzer as a system configured by a measuring section 2 and a data processing section 3, the present invention is not limited to this arrangement inasmuch as the present invention is also applicable to the analyzer management system 41 of a second modification shown in FIG. 30. The analyzer management system 41 is configured by a client computer (PC) 43 connected to a plurality of analyzers 42, a server PC 44 connected to a plurality of client PC 44, and a host PC 45 connected to a plurality of server PC 44. In the analyzer management system 41, an examination request (sample ID and examination items) are transmitted from the host PC 45 to the client PC 43 through the server PC 44. When an examination request is received, the client PC 43 issues an analysis instruction to each analyzer 42 based on the examination request, and obtains the analysis result. The client PC 43 integrates the analysis results of each analyzer 42 for each sample, and sends the data to the host PC 45. In the analyzer management system 41, the client PC 43 may also be provided with a function to display the diagnosis assisting information.

Although the above embodiment describes an example in which the blood analyzer 1 has a separate measuring section 2 and data processing section 3, the present invention is not limited to this arrangement inasmuch as the measuring section 2 and the data processing section 3 may be integrated in a single unit.

Although the above embodiment provides an example that provides diagnosis assisting information that is incorporated beforehand in an application program 304*a*, the present invention is not limited to this arrangement inasmuch as the provided information may also be edited. For example, display images and graphs may be added to the "lab result" tab, and descriptions may be added to the graphs.

Although the notification screen 150 is provided with a call button 151 to display on the diagnosis assisting information screen 200 in the above embodiment, the present invention is not limited to this arrangement inasmuch as a call button may also be provided on the analysis result display screen 100. In this case, the call button would be normally set to a non-active state, and the call button would become active when notified of the possibility that a subject had a disease. Moreover, a predetermined key of the input device 303 may be provided with a function to display the diagnosis assisting information screen 200, so that a message would notify the user to operate the key when there was a possibility that the subject had a diseased.

What is claimed is:

1. A sample analyzer, comprising:
a measuring section configured to measure characteristic information indicating a characteristic of each of particles contained in a sample collected from a subject;
a display;
a memory configured to store a predetermined condition; and
a processor programmed to perform operations comprising
obtaining an analysis result by classifying the particles into a plurality of groups and counting a number of particles included in each group, based on the characteristic information obtained by the measuring section,
creating a distribution map of the particles based on the characteristic information obtained by the measuring section,
determining whether the obtained analysis result meets the predetermined condition stored in the memory,
notifying that there is a possibility that the subject has a predetermined disease when it has been determined that the analysis result meets the predetermined condition, and
in responsive to an instruction by a user, showing, on the display, a diagnosis assisting information screen which displays a diagnosis assisting information related to the predetermined disease, wherein the diagnosis assisting information includes at least one typical distribution map of the predetermined disease and the created distribution map.

2. The sample analyzer of claim 1, wherein the diagnosis assisting information screen comprises
an attribute information display region for displaying a sample attribute information relating to an attribute of the sample;
an analysis result display region for displaying the analysis result; and
a disease information display region for displaying the diagnosis assisting information related to the predetermined disease.

3. The sample analyzer of claim 2, wherein the processor is programmed to display, in the disease information display region, at least a name of the predetermined disease, and the analysis result of an analysis item related to the predetermined disease.

4. The sample analyzer of claim 3, wherein the processor is programmed to display, in the disease assisting information display region, an information of a reference material related to the predetermined disease.

5. The sample analyzer of claim 2, wherein the processor is programmed to display, in the disease information display region, at least one typical sample image representing the characteristic of the predetermined disease.

6. The sample analyzer of claim 2, wherein the processor is programmed to display a summary of the diagnosis assisting information related to the predetermined disease in the disease information display region, and display a case of the predetermined disease in the disease information display region.

7. The sample analyzer of claim 1, wherein the memory is configured to store determination results by the processor,
and wherein the processor is programmed to execute a notification when a determination result based on the analysis result of the subject is different from a determination result based on a previous analysis result of the subject stored in the memory.

8. The sample analyzer of claim 1, wherein the processor is programmed to show, on the display, a calling screen for receiving a call instruction to call up the diagnosis assisting information screen, and show the diagnosis assisting information screen in responsive to the call up instruction through the calling screen.

9. The sample analyzer of claim 8, wherein the processor is programmed to show the calling screen together with the analysis result.

10. The sample analyzer of claim 1, wherein
the memory is configured to store the predetermined condition with the diagnosis assisting information related to the predetermined disease.

11. The sample analyzer of claim 1, wherein
the characteristic information includes at least one of a forward scattered light, a side scattered light and a fluorescent light generated from each of the particles.

12. The sample analyzer of claim 1, wherein
the analysis result includes a number of lymphocytes, a number of monocytes, a number of neutrophils, a number of eosinophils, a number of basophils, a number of red blood cells, a number of platelets, a number of reticulocytes, a number of immature platelets, and a hemoglobin value.

13. A diagnosis assisting information providing device comprising:
a display;
a memory configured to store a predetermined condition; and
a processor programmed to perform operations comprising
obtaining an analysis result of a sample collected from a subject and a distribution map of particles contained in the sample, wherein the analysis result is generated by classifying the particles into a plurality of groups and counting a number of particles included in each group;
determining whether the obtained analysis result meets the predetermined condition stored in the memory;
notifying that there is a possibility that the subject has a predetermined disease when it has been determined that the analysis result meets the predetermined condition; and
in responsive to an instruction by a user, showing, on the display, a diagnosis assisting information screen which displays a diagnosis assisting information related to the predetermined disease, wherein the diagnosis assisting information includes at least one typical distribution map of the predetermined disease and the obtained distribution map of the subject.

14. A non-transitory storage medium which stores programs executable collectively by at least one processor to:
obtain an analysis result of a sample collected from a subject and a distribution map of particles contained in the sample, wherein the analysis result is generated by classifying the particles into a plurality of groups and counting a number of particles included in each group;
determine whether the obtained analysis result meets a predetermined condition stored in the non-transitory storage medium;
notify that there is a possibility that the subject has a predetermined disease when it has been determined that the analysis result meets the predetermined condition; and
in responsive to an instruction by a user, show a diagnosis assisting information screen which displays a diagnosis assisting information related to the predetermined disease, wherein the diagnosis assisting information includes at least one typical distribution map of the predetermined disease and the obtained distribution map of the subject.

* * * * *